US011861625B2

(12) United States Patent
Ashtekar et al.

(10) Patent No.: US 11,861,625 B2
(45) Date of Patent: Jan. 2, 2024

(54) METHOD AND SYSTEM FOR CARBON FOOTPRINT MONITORING BASED ON REGENERATIVE PRACTICE IMPLEMENTATION

(71) Applicant: CIBO Technologies, Inc., Cambridge, MA (US)

(72) Inventors: Jenette M. Ashtekar, Weston, MA (US); Pankaj C. Bhambhani, Malden, MA (US); Ernesto Brau, Newton, MA (US); Marie A. Coffin, Cary, NC (US); Margaret C. Kosmala, Acton, MA (US)

(73) Assignee: CIBO Technologies, Inc., St. Louis Park, MN (US)

( * ) Notice: Subject to any disclaimer, the term of this patent is extended or adjusted under 35 U.S.C. 154(b) by 494 days.

(21) Appl. No.: 17/085,056

(22) Filed: Oct. 30, 2020

(65) Prior Publication Data

US 2022/0138767 A1    May 5, 2022

(51) Int. Cl.
*G06Q 30/018* (2023.01)
*G06Q 10/067* (2023.01)
(Continued)

(52) U.S. Cl.
CPC ....... *G06Q 30/0185* (2013.01); *A01B 79/005* (2013.01); *A01G 25/16* (2013.01);
(Continued)

(58) Field of Classification Search
CPC ......... G06Q 30/0185; G06Q 10/06312; G06Q 10/067; G06Q 50/02; G06Q 30/0201;
(Continued)

(56) References Cited

U.S. PATENT DOCUMENTS 9,524,463 B2    12/2016  Meinrenken et al.
9,665,907 B2     5/2017  Hamilton, II et al.
(Continued)

FOREIGN PATENT DOCUMENTS

WO    WO2013088232    6/2013
WO    WO2022081180    4/2022

OTHER PUBLICATIONS

McCombs, Representing the Relationships Between Field Collected Carbon Exchanges and Surface Reflectance Using Geospatial and Satellite-Based Techniques, PhD diss., University of South Carolina (2017) (Year: 2017).*

(Continued)

*Primary Examiner* — Charles Guiliano
(74) *Attorney, Agent, or Firm* — Richard K. Huffman; Huffman Patent Group, LLC

(57) ABSTRACT

A method for monitoring regenerative management practices in agricultural parcels includes: determining a regenerative carbon footprint value for a parcel that comprises a difference of a regenerative carbon footprint and a baseline carbon footprint, where the baseline carbon footprint is derived by calculating greenhouse gas emissions based on simulating crop growth under current management practices and the regenerative carbon footprint is derived by calculating greenhouse gas emissions based on simulating crop growth under one or more regenerative management practices; for key dates corresponding to implementation and maintenance of each of the one or more regenerative management practices, processing and evaluating remotely sensed images against corresponding crop curves to determine compliance/noncompliance indicators that correspond each of the key dates; and storing the compliance/noncompliance indicators within a parcel database, where the compliance/noncompliance indicators are employed at a final (Continued)

date to verify implementation and maintenance of the one or more regenerative management practices.

20 Claims, 16 Drawing Sheets

(51) Int. Cl.
| | |
|---|---|
| *G06Q 10/0631* | (2023.01) |
| *G01N 21/27* | (2006.01) |
| *G01N 33/00* | (2006.01) |
| *A01G 25/16* | (2006.01) |
| *A01B 79/00* | (2006.01) |
| *G06Q 50/02* | (2012.01) |
| *G06V 20/10* | (2022.01) |
| *G06T 7/00* | (2017.01) |
| *G06Q 40/04* | (2012.01) |
| *G06Q 50/26* | (2012.01) |
| *G06Q 30/0201* | (2023.01) |

(52) U.S. Cl.
CPC ........... *G01N 21/27* (2013.01); *G01N 33/004* (2013.01); *G01N 33/0037* (2013.01); *G06Q 10/067* (2013.01); *G06Q 10/06312* (2013.01); *G06Q 50/02* (2013.01); *G06T 7/0004* (2013.01); *G06V 20/188* (2022.01); *G06Q 30/0201* (2013.01); *G06Q 40/04* (2013.01); *G06Q 50/26* (2013.01); *G06T 2207/10024* (2013.01); *G06T 2207/30188* (2013.01)

(58) Field of Classification Search
CPC ...... G06Q 40/04; G06Q 50/26; G06V 20/188; A01B 79/005; A01G 25/16; G01N 21/27; G01N 33/0037; G01N 33/004; G06T 7/0004; G06T 2207/10024; G06T 2207/30188
USPC ...................................................... 705/7.22
See application file for complete search history.

(56) References Cited

U.S. PATENT DOCUMENTS

| | | |
|---|---|---|
| 2004/0015454 A1 | 1/2004 | Raines et al. |
| 2008/0177605 A1 | 7/2008 | Zimmerman |
| 2008/0201255 A1 | 8/2008 | Green |
| 2009/0043653 A1 | 2/2009 | Sandor et al. |
| 2009/0144096 A1 | 6/2009 | Andrilenas et al. |
| 2009/0171975 A1 | 7/2009 | Mcconnell et al. |
| 2009/0326715 A1* | 12/2009 | Liska .................... G06Q 10/10 700/266 |
| 2011/0087578 A1 | 4/2011 | Finck et al. |
| 2011/0213690 A1 | 9/2011 | Ghosh et al. |
| 2011/0313666 A1* | 12/2011 | Hirvi ..................... A01G 22/00 702/2 |
| 2012/0290140 A1 | 11/2012 | Groeneveld |
| 2018/0075546 A1* | 3/2018 | Richt ..................... G06T 1/0007 |
| 2018/0242539 A1 | 8/2018 | Bhattacharya et al. |
| 2018/0368338 A1 | 12/2018 | Jerphagnon et al. |
| 2019/0335674 A1 | 11/2019 | Basso |
| 2020/0027096 A1 | 1/2020 | Cooner |
| 2021/0199600 A1* | 7/2021 | Das ....................... G01N 22/04 |
| 2021/0209490 A1 | 7/2021 | Casas |
| 2022/0114562 A1 | 4/2022 | Oliver Gomila |

OTHER PUBLICATIONS

Ayaz, Muhammad et al. "Internet-of-Things (IoT)-Based Smart Agriculture: Toward Making the Fields Talk." in IEEE Access. vol.7. Special Section on New Technologies for Smart Farming 4.0; Research Challenges and Opportunities. Sep. 23, 2019. pp. 129551-129583.

Casas, Angeles et al. "Using Optical Remote Sensors and Machine Learning Models to Predict Agronomic Field Property Data." U.S. Appl. No. 62/958,211, filed Jan. 7, 2020, related to PG Pub US 20210209490 A1.

Maheshwari, Aditi et al. "Automating and Analyzing Whole-Farm Carbon Models." 2020 IEEE 7th International Conference on Data Science and Advanced Analytics (DSAA). Sydney, NSW, Australia. 2020 pp. 429-438. DOI: 10.1109/DSAA49011.2020.00057.

* cited by examiner

FIG. 3  SYSTEM LEVEL FLOW FOR GENERATION OF CARBON FOOTPRINT AND REGENERATIVE POTENTIAL

*MANAGEMENT PRACTICES SCENARIO BUILDER FLOW*

EXEMPLARY CARBON OFFSETS OFFER DISPLAY

EXEMPLARY DETAILED CARBON FOOTPRINT COMPARISON DISPLAY — 1300

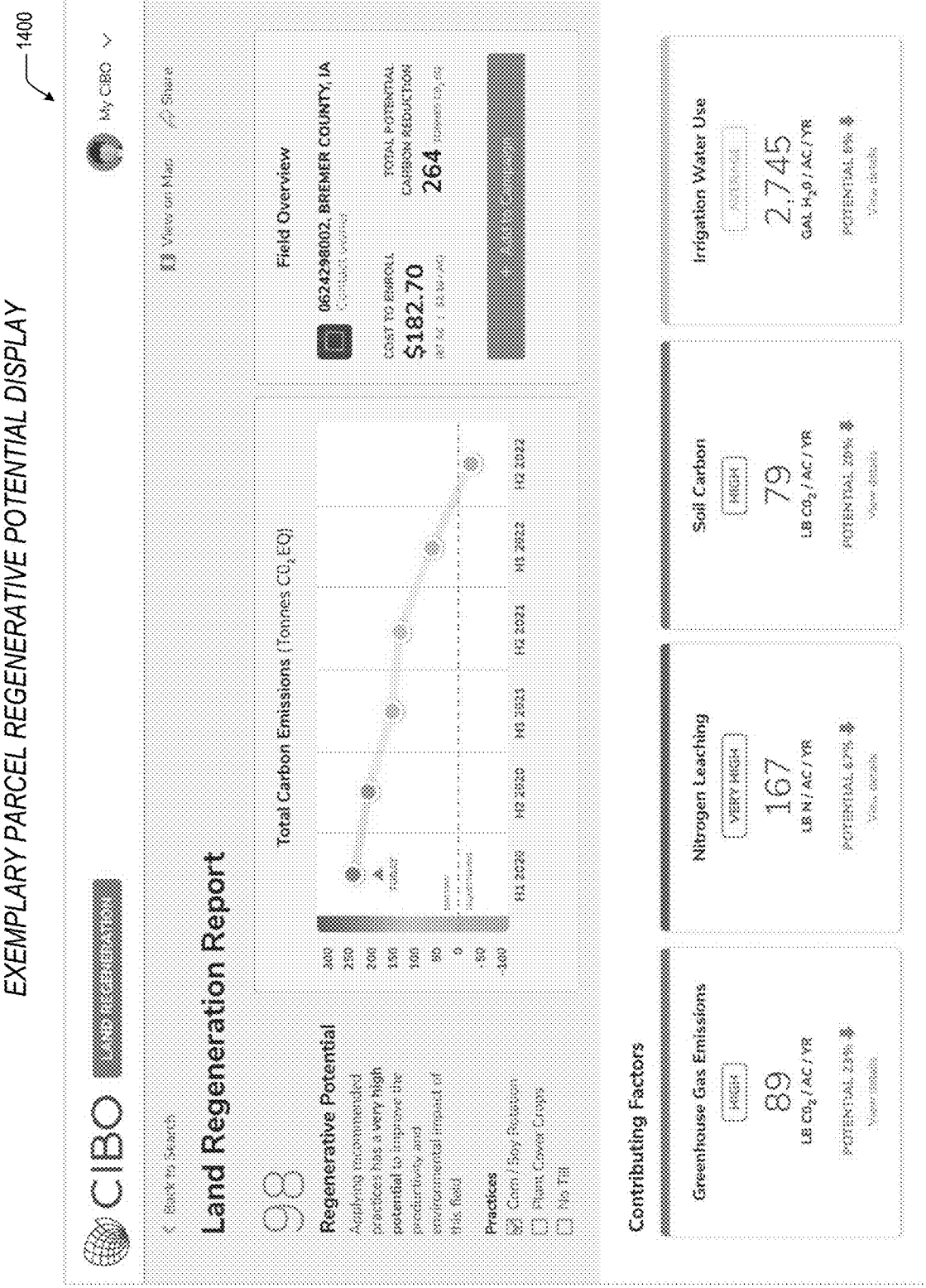
FIG. 14 — EXEMPLARY PARCEL REGENERATIVE POTENTIAL DISPLAY

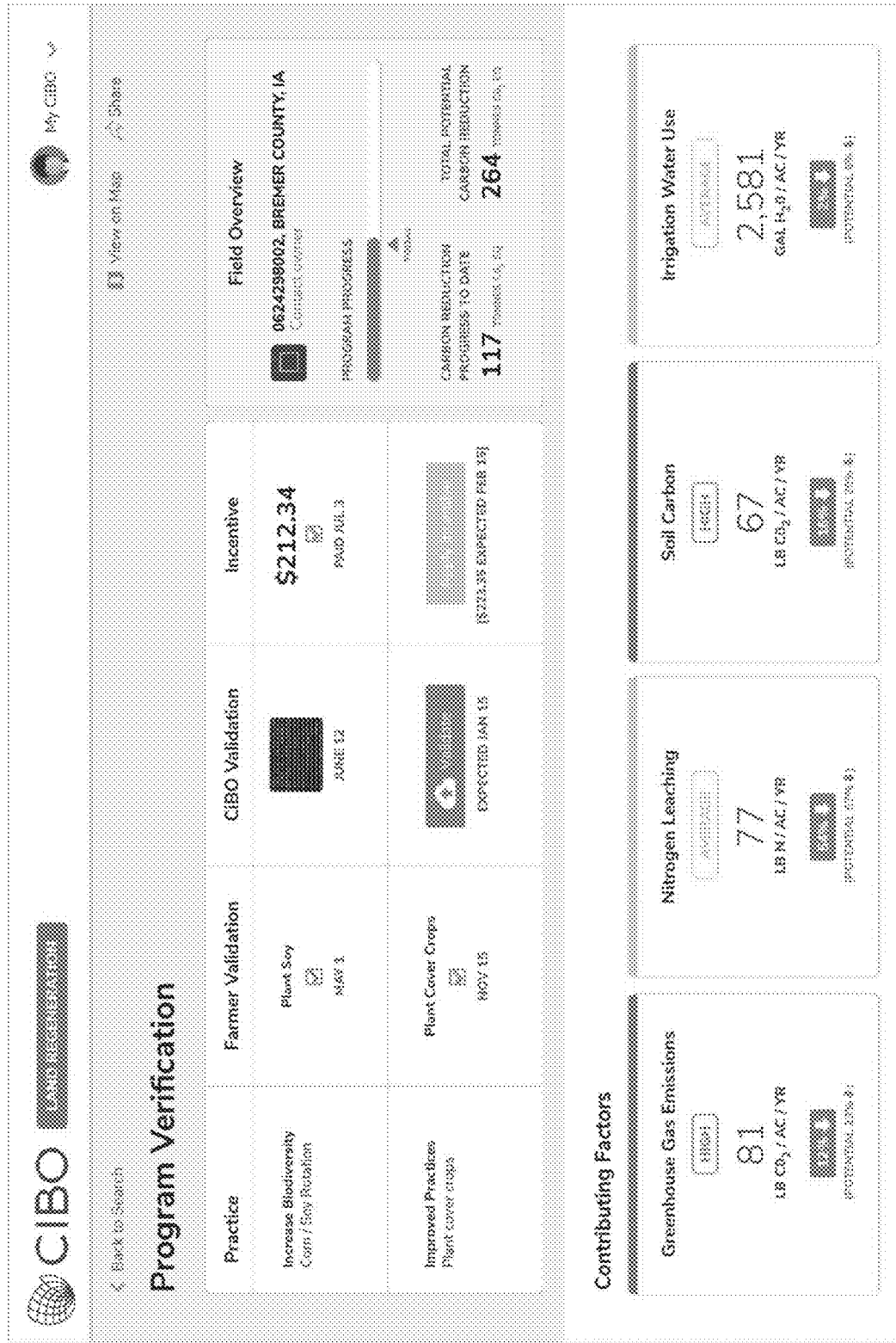
FIG. 15     EXEMPLARY CARBON SEQUESTRATION PROGRESS DISPLAY

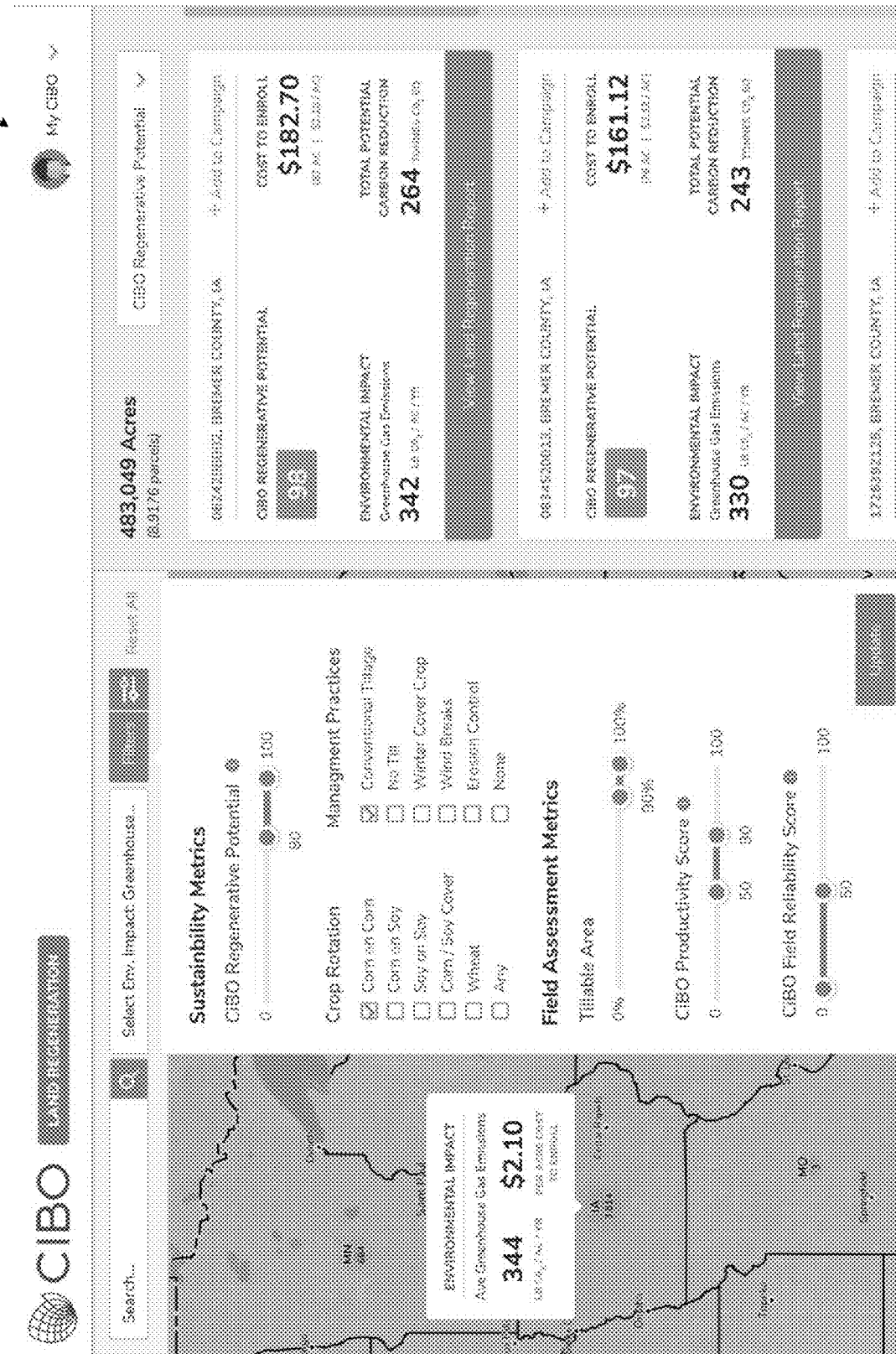
FIG. 16 EXEMPLARY PARCEL SEARCH RESULTS DISPLAY

US 11,861,625 B2

METHOD AND SYSTEM FOR CARBON FOOTPRINT MONITORING BASED ON REGENERATIVE PRACTICE IMPLEMENTATION

CROSS-REFERENCE TO RELATED APPLICATIONS

This application is related to the following co-pending U.S. patent applications, each of which has a common assignee and common inventors, the entireties of which are herein incorporated by reference.

| SERIAL NUMBER | FILING DATE | TITLE |
| --- | --- | --- |
| (CIBO.2010) | — | METHOD AND SYSTEM FOR CARBON FOOTPRINT DETERMINATION BASED ON REGENERATIVE PRACTICE IMPLEMENTATION |
| (CIBO.2012) | — | METHOD AND SYSTEM FOR VERIFICATION OF CARBON FOOTPRINT IN AGRICULTURAL PARCELS |

BACKGROUND OF THE INVENTION

Field of the Invention

This invention relates in general to the field of regenerative agricultural practices, and more specifically to methods and systems for carbon footprint determination, monitoring, and verification for agricultural parcels based on implementation of regenerative management practices.

Description of the Related Art

Climate change is one of the most studied and discussed topics on the planet, and this level of global concern has sparked numerous initiatives to reduce Earth's carbon footprint. Initiatives include zero waste recycling and reuse programs, clean energy programs, conservation measures, sustainable transportation programs, and carbon offset and trading programs. This application focuses on carbon offsets from an agricultural perspective, how they are determined, and how programs to generate those offsets are monitored and verified.

As one skilled in the art will appreciate, billions of dollars are spent each year by countries, corporations, small businesses, and individuals to reduce greenhouse gas emissions. But more often than not, the impact of carbon footprint reduction programs is difficult to quantify. Airlines purchase carbon credits to assuage public reaction to the amount of greenhouse gas emissions associated with each flight. Consumer product companies invest in carbon credits in order to advertise that they are committed to reducing, eliminating, and reversing their carbon footprint. Politicians mandate production of products and modes of transportation that will reduce greenhouse gas emissions. And individuals make choices for which products (e.g., clothing, electricity, food) they will purchase based upon their desire to be better stewards of the planet. But, the problem is that these investments in carbon credits tend more toward a feel-good narrative rather than a do-good narrative, primarily because it is difficult to estimate the amount of carbon footprint reduction associated with a credit, to monitor a carbon footprint reduction activity to ensure that it is implemented and maintained in exchange for the price of the credit, and to ultimately verify that the amount of carbon footprint reduction advertised with the carbon credit has actually been achieved. These challenges are amplified when viewed from an agricultural perspective.

Growers (individual farmers to conglomerates) want to make a profit, but they are also motivated to reduce greenhouse gas emissions from their farms, particularly if these reductions will result in increases in productivity and sustainable production over time. Yet, because reductions in carbon footprints are hard to estimate, they tend to implement well known regenerative practices such as crop rotation and cover cropping, and they forego more forward looking regenerative practices such as low-till/low-till, low nitrogen content fertilization, etc., primarily because the carbon footprint impact of most regenerative agricultural management practices cannot be accurately determined. In addition, growers may be subject to acceptance of lower-priced incentives to implement regenerative management practices simply because of this accuracy problem.

The process of translating regenerative management practices into farmer incentives and carbon credit valuations is currently labor intensive. In a typical scenario, an agronomist from, say, a consumer products company is sent out to the field of a grower who is interested in regenerative agriculture. The agronomist queries the farmer about baseline management practices and then estimates how much carbon can be sequestered under one or more regenerative practices using rule-of-thumb calculations. Market conditions for the region and crop type will dictate pricing of incentives and associated carbon credits (if the credits are brokered). And compliance verification is generally based on the honor system or is observed in-person by representatives of the company that provided the incentives to the grower.

Therefore, what is needed are automated methods and systems that enable growers and carbon credit purchasers to correctly determine the carbon footprint of a field under the grower's current ("baseline") management practices and to accurately predict the reduction of greenhouse gas emissions associated with implementation of one or more regenerative practices.

What is also needed are automated methods and systems for monitoring implementation and maintenance of regenerative management practices on a farm or group of farms where compliance progress does not require self-reporting or onsite evaluations.

What is further needed are automated methods and systems for verifying compliance with implemented regenerative practices to trust that the amount of carbon sequestered by those implemented regenerative practices is equivalent to that offered in purchased carbon credits.

SUMMARY OF THE INVENTION

The present invention, among other applications, is directed to solving the above-noted problems and addresses other problems, disadvantages, and limitations of the prior art by providing a superior technique for employing a combination of public data, commercial data, field trial data, and crop simulation data to determine, monitor, and verify the potential and effectiveness of regenerative management practices and to generate agro-economic metrics and objective valuations for a vast number of agricultural parcels. In one embodiment, a method for monitoring implementation and maintenance of regenerative management practices in agricultural parcels is provided, the method including: determining a regenerative carbon footprint value for a parcel, where the determining comprises a difference of a regenerative carbon footprint and a baseline carbon footprint, where the baseline carbon footprint is derived by calculating greenhouse gas emissions based on simulating crop growth under current management practices, and where the regenerative carbon footprint is derived by calculating greenhouse gas emissions based on simulating crop growth under one or more regenerative management practices; for key dates corresponding to implementation and maintenance of each of the one or more regenerative management practices, processing and evaluating remotely sensed images against corresponding crop curves to determine compliance/noncompliance indicators that correspond each of the key dates; and storing the compliance/noncompliance indicators within a parcel database, where the compliance/noncompliance indicators are employed at a final date to verify implementation and maintenance of the one or more regenerative management practices.

One aspect of the present invention contemplates a computer-readable storage medium storing program instructions that, when executed by a computer, cause the computer to perform a method for monitoring implementation and maintenance of regenerative management practices in agricultural parcels, the method including: determining a regenerative carbon footprint value for a parcel, where the determining comprises a difference of a regenerative carbon footprint and a baseline carbon footprint, where the baseline carbon footprint is derived by calculating greenhouse gas emissions based on simulating crop growth under current management practices, and where the regenerative carbon footprint is derived by calculating greenhouse gas emissions based on simulating crop growth under one or more regenerative management practices; for key dates corresponding to implementation and maintenance of each of the one or more regenerative management practices, processing and evaluating remotely sensed images against corresponding crop curves to determine compliance/noncompliance indicators that correspond each of the key dates; and storing the compliance/noncompliance indicators within a parcel database, where the compliance/noncompliance indicators are employed at a final date to verify implementation and maintenance of the one or more regenerative management practices.

Another aspect of the present invention envisages a system for monitoring implementation and maintenance of regenerative management practices in agricultural parcels, the system including: a CO2E sequestration server, including: a CO2E management processor, configured to determine a regenerative carbon footprint value for a parcel, where the regenerative carbon footprint value comprises a difference of a regenerative carbon footprint and a baseline carbon footprint, and where the baseline carbon footprint is derived by calculating greenhouse gas emissions based by employing a crop simulation processor to simulate crop growth under current management practices, and where the regenerative carbon footprint is derived by calculating greenhouse gas emissions based on employing the crop simulation processor to simulate crop growth under one or more regenerative management practices; and a CO2E determination processor, for key dates corresponding to implementation and maintenance of each of the one or more regenerative management practices, configured to process and evaluate remotely sensed images provided by a remote sense processor against corresponding crop curves to determine compliance/noncompliance indicators that correspond each of the key dates, and configured to store the compliance/noncompliance indicators within a parcel database, where the compliance/noncompliance indicators are employed at a final date to verify the implementation and maintenance of the one or more regenerative management practices.

BRIEF DESCRIPTION OF THE DRAWINGS

These and other objects, features, and advantages of the present invention will become better understood with regard to the following description and accompanying drawings where:

FIG. 14 is a diagram illustrating an exemplary parcel regenerative potential display according to the present invention such as might be presented by the client device of FIG. 11;

FIG. 15 is a diagram detailing an exemplary carbon sequestration progress display according to the present invention such as might be presented by the client device of FIG. 11; and FIG. 16 is a diagram detailing an exemplary parcel search results display according to the present invention such as might be presented by the client device of FIG. 11.

DETAILED DESCRIPTION

Figure 1:
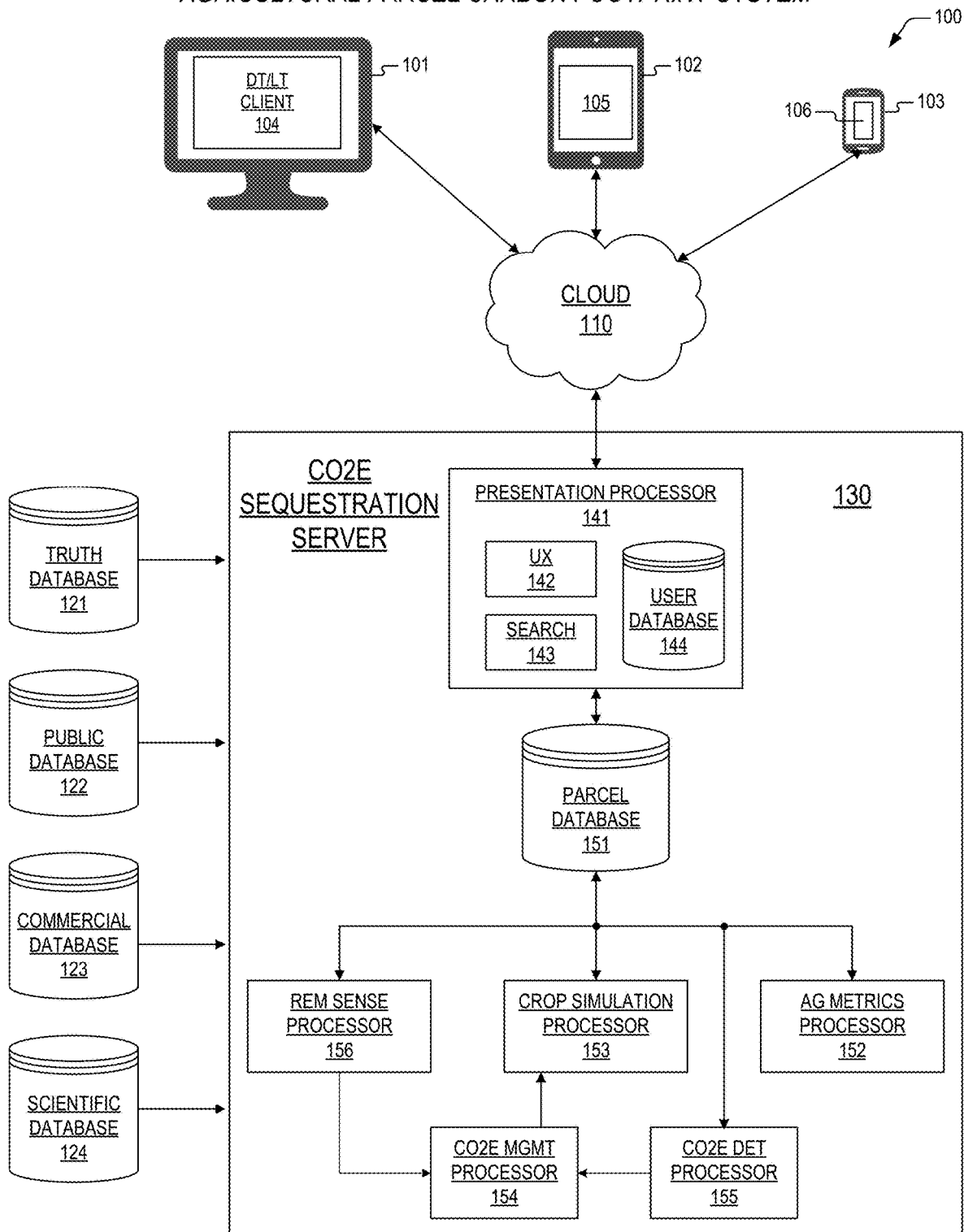
FIG. 1 is a block diagram illustrating an agricultural parcel carbon footprint system according to the present invention.

Exemplary and illustrative embodiments of the invention are described below. It should be understood at the outset that, although exemplary embodiments are illustrated in the figures and described below, the principles of the present disclosure may be implemented using any number of techniques, whether currently known or not. In the interest of clarity, not all features of an actual implementation are described in this specification, for those skilled in the art will appreciate that in the development of any such actual embodiment, numerous implementation-specific decisions are made to achieve specific goals, such as compliance with system-related and business-related constraints, which vary from one implementation to another. Furthermore, it will be appreciated that such a development effort might be complex and time-consuming, but would nevertheless be a routine undertaking for those of ordinary skill in the art having the benefit of this disclosure. Various modifications to the preferred embodiment will be apparent to those skilled in the art, and the general principles defined herein may be applied to other embodiments. Therefore, the present invention is not intended to be limited to the particular embodiments shown and described herein but is to be accorded the widest scope consistent with the principles and novel features herein disclosed.

The present invention will now be described with reference to the attached figures. Various structures, systems, and devices are schematically depicted in the drawings for purposes of explanation only and so as to not obscure the present invention with details that are well known to those skilled in the art. Nevertheless, the attached drawings are included to describe and explain illustrative examples of the present invention. Unless otherwise specifically noted, articles depicted in the drawings are not necessarily drawn to scale.

The words and phrases used herein should be understood and interpreted to have a meaning consistent with the understanding of those words and phrases by those skilled in the relevant art. No special definition of a term or phrase (i.e., a definition that is different from the ordinary and customary meaning as understood by those skilled in the art) is intended to be implied by consistent usage of the term or phrase herein. To the extent that a term or phrase is intended to have a special meaning (i.e., a meaning other than that understood by skilled artisans) such a special definition will be expressly set forth in the specification in a definitional manner that directly and unequivocally provides the special definition for the term or phrase. As used in this disclosure, "each" refers to each member of a set, each member of a subset, each member of a group, each member of a portion, each member of a part, etc.

Applicants note that unless the words "means for" or "step for" are explicitly used in a particular claim, it is not intended that any of the appended claims or claim elements are recited in such a manner as to invoke 35 U.S.C. § 112(f).

DEFINITIONS

Greenhouse Gases: The different gases that cause the "greenhouse effect" in Earth's atmosphere, basically causing light from the sun to be trapped as heat. The most important gases to consider for row crop agriculture are carbon dioxide ($CO_2$) and nitrous oxide ($N_2O$).

Greenhouse Gas Emissions: The various human activities that emit, or release, greenhouse gases into the air. For example, driving a car burns fossil fuels which releases $CO_2$ as a byproduct. In agricultural parcels, emissions occur directly from the soil as a result of soil management, from performing necessary farming activities (e.g., driving tractors, which burn fossil fuels, releasing $CO_2$), and from manufacturing nitrogen fertilizer (which also burns fossil fuels, releasing $CO_2$).

Carbon Sequestration: The amount of additional carbon is retained in the soil. In some cases, the amount of carbon in the soil increases over time and such is referred to as the amount of carbon that is being sequestered. If the amount of carbon in the soil is decreasing over time (i.e., being released into the atmosphere as $CO_2$), then such is referred to as a greenhouse gas emission. In any given calculation for a field, carbon is either being sequestered or emitted.

CO2e (or CO2E): A single number representing the greenhouse gas impact of the different gasses forming the greenhouse effect, where gases other than $CO_2$ are converted into carbon dioxide equivalents using standard conversion techniques prescribed by the Intergovernmental Panel on Climate Change (IPCC) that are based on the effects of each of the gasses in the atmosphere.

Carbon Footprint: A single number expressed in CO2e that represents the aggregation of both greenhouse gas emissions and carbon sequestration occurring in a single field (or prescribed region, etc.). Since both greenhouse gas emissions and carbon sequestration may be converted to CO2e, a field's net total greenhouse gas emissions (i.e., greenhouse gas emissions minus carbon sequestration) is referred to as it's carbon footprint.

Central Processing Unit (CPU): The electronic circuits (i.e., "hardware") that execute the instructions of a computer program (also known as a "computer application," "application," "application program," "app," "computer program," or "program") by performing operations on data, where the operations may include arithmetic operations, logical operations, or input/output operations. A CPU may also be referred to as a "processor."

Module: As used herein, the term "module" may refer to, be part of, or include an application specific integrated circuit (ASIC), an electronic circuit, a processor (shared, dedicated, or group) and/or memory (shared, dedicated, or group) that execute one or more computer programs, a combinational logic circuit, and/or other suitable components that provide the described functionality.

In view of the above background discussion on how agencies determine and assign carbon offset credits to particular regenerative practices along with how implementation of those practices is tracked, a discussion of the present invention will be provided with reference to FIGS. 1-16. The present invention overcomes the problems associated with present-day carbon offsets techniques by providing automated methods and systems directed toward determining the regenerative potential of an agricultural parcel in tons of carbon dioxide equivalent (CO2E) when that parcel is managed according to one or more best regenerative management practices compared to current, baseline management practices. These automated methods and systems may also be employed to monitor progress of the one or more best regenerative management practices over an implementation period, and my further be employed to verify that implementation of the one or more best regenerative management practices resulted in sequestration of the amount of CO2E that was previously determined.

Referring to FIG. 1, a block diagram is presented illustrating an agricultural parcel carbon footprint system 100 according to the present invention. The system 100 may include a carbon dioxide equivalent (CO2E) sequestration server 130 that is coupled to one or more client devices 101-103 through the internet cloud 110. The client devices 101-103 may include one or more desktop/laptop computers 101 that execute desktop/laptop client applications 104 for communication and interaction with the CO2E sequestration server 130 through the internet cloud 110. The client devices 101-103 may also include one or more smart tablet computers 102 that execute tablet client applications 105 for communication and interaction with the CO2E sequestration server 130 through the internet cloud 110. The client devices 101-103 may further include one or more smartphone devices 103 that execute smartphone client applications 106 for communication and interaction with the CO2E sequestration server 130 through the internet cloud 110.

The CO2E sequestration server 130 is coupled to a truth database 121, a public database 122, a commercial database 123, and a scientific database 124. Though represented in the block diagram as single databases 121-124, each of the databases 121-124 may comprise a substantial number of databases through which the CO2E sequestration server 130 may access truth-based data, public data, commercial data, and scientific data in order to translate this data into carbon footprints and carbon sequestration resulting from regenerative management practices into agriculturally meaningful metrics and valuations for a vast number of agricultural parcels.

Preferably, truth-based data includes data obtained directly from growers and may include "as applied" data corresponding to fertilizer application and field trial results, namely, the measurements taken by farming partners who plant and harvest crops under a wide range of specified scenarios. These field trial results are employed by the CO2E sequestration server 130 to test and improve the accuracy of crop simulations that may be performed to generate baseline and regenerative practices carbon footprints and to translate these footprints into agriculturally meaningful metrics and valuations for similar parcels, where such translations are employed to scale simulations from individual parcels to hundreds of thousands of parcels within geographic regions.

Public data comprises a wide variety of sources such as, but not limited to, county records, United States Department of Agriculture reports; parcel geographic coordinates data and topography; soil types and layering (e.g., Soil Survey Geographic Database (SSURGO); historical crop planting, harvesting, and yield data; soil type indexes (e.g., Corn Stability Rating 2 (CSR2); historical and forecast weather data; and satellite and aerial image data taken across agriculturally meaningful spectral bands (e.g., LANDSAT, SENTINEL) that may be processed by the CO2E sequestration server 130 to understand crop types, rotations, baseline management practices (e.g., planting dates, tillage types and dates, fertilization types and dates, irrigation types and dates, harvesting dates), and stages of growth at any given time.

Commercial data may comprise any of the public data that is aggregated or formatted for ease of access by the CO2E sequestration server 130.

Scientific data may comprise selected results of global scientific results taken from published literature. The results are provided to the CO2E sequestration server 130 to validate crop simulations and to ensure that the simulations are accurate across a wide range of management scenarios and weather conditions. In one embodiment, crop simulation results are compared to scientific research data obtained under similar management practices and weather conditions.

The CO2E sequestration server 130 may include a presentation processor 141 that is coupled to a parcel database 151. The presentation processor 141 comprises a user interface (UX) component 142, a search engine component 143, and a user database 144.

The CO2E sequestration server 130 may further comprise an agricultural metrics processor 152, a crop simulation processor 153, a CO2E detection processor 155, and a remote sense processor 156, all of which are coupled to the parcel database 151. The CO2E sequestration server 130 may further comprise a CO2E management processor 154 that is coupled to the CO2E detection processor 155, the remote sense processor 157, and the crop simulation processor 153.

In operation, records corresponding to agricultural parcels in a prescribed region are created, iterated, and revised as a function of newly available data from one or more of the databases 121-124 and applicable results from recent crop simulations performed by the crop simulation processor 153. The records are stored in the parcel database 151 for access by the agricultural metrics processor 152, remote sense processor 156, the CO2E detection processor 155, and the presentation processor 141. Users may execute the client applications 104-106 on the client devices 101-103 to specify constraints, weights, and search parameters for one or more parcel records stored within the parcel database 151 and to enter parameters corresponding to proposed regenerative management practices for parcels that they manage. The user interface processor 142 executes in order to transmit display and data entry windows to the client devices 101-103 via their respective client applications 104-106 to enable the users to specify the constraints, weights, and search parameters and to enter the parameters corresponding to the proposed regenerative management practices. The client applications 104-106 may transmit the constraints, weights, search, and regenerative practices parameters to the presentation processor 141 through the internet cloud 141. In one embodiment, the constraints, weights, search, and regenerative practices parameters are stored in corresponding user records within the user database 144 to accelerate subsequent searches. Upon receipt of the constraints, weights, search, and regenerative practices parameters, the search engine processor 143 employs the corresponding user records to access one or more records within the parcel database 151 that satisfy the constraints, weights, search, and regenerative practices parameters. The one or more records within the parcel database 151 that satisfy the constraints, weights, search, and regenerative practices parameters may also be stored in corresponding user records within the user database 144 to accelerate subsequent searches, and the one or more records within the parcel database 151 that satisfy the constraints, weights, search, and regenerative practices parameters are provided by the search engine processor 143 to the user interface processor 142, which formats the one or more records for display by the client applications 104-106 on the client devices 101-103 according to device type, and the presentation processor 141 transmits the one or more records to the client devices 101-103 along with contextual metadata corresponding to the one or more parcels (e.g., parcels shown on a map) that enable the users to visualize and better comprehend results of their searches.

In one embodiment, users may iteratively refine searches by specifying additional constraints, weights, search, and regenerative practices parameters to further target search results that are of interest, and these results are additionally stored in the corresponding user records within the user database 144.

Upon selection of a specific parcel record, the presentation processor 141 may transmit fields within the records that are formatted by the user interface processor 142 for display to the user along with metadata that enable the user to visualize and comprehend the record fields associated with the parcel, thus providing the user with a substantially improved method for making an informed decision regarding a corresponding agricultural parcel based upon user category (e.g., small farmer, enterprise farming corporation, underwriter, lender, insurer, etc.).

The remote sense processor 156 may process satellite/aerial images, and may merge selected images to determine vegetative indices, to estimate missing image data, and to determine both baseline management practices and the amount of CO2E that may be sequestered under one or more best management practices when compared to the baseline management practices for the parcel. In addition, the remote sense processor 156 in conjunction with the CO2E detection processor 155 may additionally employ machine learning and computer vision techniques, described in further detail below, to infer implementation and maintenance of one or more regenerative management practices.

The CO2E management practices processor 154 may access data from the databases 121-124 corresponding to baseline management practices associated with parcels and rank the outputs against other management practice data that is received from one or more of the databases 121-124. In turn, the management practices processor 154 may augment sparse or incomplete data in order to provide location-specific inferences for a number of key crop management practices including, but not limited to planted crop type, specific cultivar or crop variety, planting data, planting density (i.e., seeds per acre and row spacing), tillage, fertilizer application (e.g., dates and amounts), and irrigation (e.g., dates and amounts). In one embodiment, highest ranked management practices are employed to construct simulation inputs to the crop simulation processor 153 for modeling of required multi-year crop simulations. For example, management practices from the truth database 121 may be ranked higher than crop simulation results. In the absence of truth data for a parcel, state guidelines or management practices rules of thumb may be employed to build directives for simulations. The CO2E management practices processor 154 may further access data from the databases 121-124 to determine one or more regenerative management practices (e.g., crop species and maturity; planting dates; crop rotation; cover cropping; tillage type; fertilizer type, amount, and timing; and irrigation amount and timing), where the one or more regenerative management practices are employed to construct simulation inputs to the crop simulation processor 153 for modeling of regenerative multi-year crop simulations in order to accurately determine the amount of carbon that may be sequestered over baseline field management.

The results of the crop simulations and remotely sensed images may be employed by the CO2E detection processor 155 to determine the carbon sequestration potential for parcels in the parcel database 151. The results may also be employed by the agricultural metrics processor 152 to iteratively translate simulation results and data provided by the databases 121-124 into figures of merit (e.g., field productivity, field production stability, field regenerative potential) and an agricultural valuation for every parcel within the parcel database 151. In one embodiment, the number of parcel records in the parcel database 151 comprises in excess of 20 million parcels located in the United States. Though the present disclosure employs terminology and examples focused on the United States, the present inventors note that such terminology and examples are provided only to clearly teach aspects of the present invention, and that the present invention may be easily modified to covers like embodiments in any other country or countries in the world.

The results of the crop simulations may be further be employed by the remote sense processor 156 to establish regenerative practices attributes (e.g., crop type and maturity of a field for which a grower has implemented one or more regenerative management practices) that must be exhibited on or about corresponding regenerative practices implementation milestones in order to automatically monitor the grower's progress and to verify implementation of the one or more regenerative management practices at the end of a growing season, thereby enabling financial incentives to be paid to the grower for implementing the one or more regenerative management practices and to accurately confirm that carbon credits reserved by purchasers have been realized.

In one embodiment, the crop simulation processor 153 preferably comprises a mechanistic crop model such as the Systems Approach to Land Use Suitability (SALUS), the initial version of which was developed at Michigan State University and which has been the subject of 20 years of testing across hundreds of fields in 46 countries, more than 25 PhD dissertations, over 200 peer-reviewed journal articles, and thousands of academic citations. It is not the purpose of the present application to provide an in depth tutorial on mechanistic crop modeling, but rather to disclose how results of crop simulations performed by crop simulation processor 153 are employed to determine the carbon sequestration potential for parcels and how the results are translated into agriculturally meaningful metrics that enables a user to make informed and meaningful decisions for one or more parcels. For a tutorial on SALUS, the reader is directed to the publications below:

Basso, B., & Ritchie, J. T. (2015). Simulating crop growth and biogeochemical fluxes in response to land management using the SALUS model. In S. K. Hamilton, J. E. Doll, & G. P. Robertson (Eds.), *The ecology of agricultural landscapes: long-term research on the path to sustainability*. New York, NY, USA: Oxford University Press, 252-274;

Basso, B., Ritchie, J. T., Grace, P. R., Sartori, L. (2006). Simulation of tillage systems impact on soil biophysical properties using the SALUS model. *Italian Journal of Agronomy*, 1(4), 677. doi: 10.4081/ija.2006.677;

Albarenque, S. M., Basso, B., Caviglia, O. P., Melchiori, R. J. (2016). Spatio-temporal nitrogen fertilizer response in maize: field study and modeling approach. *Agronomy Journal*, 108(5), 2110. doi: 10.2134/agronj2016.02.0081; and Partridge, T. F., Winter, J. M., Liu, L., Kendall, A. D., Basso, B., Hydnman, D. (2019). Mid-20th century warming hole boosts U.S. maize yields. *Environmental Research Letters*. doi: 10.1088/1748-9326/ab422b The present inventors note that the crop simulation processor 153 according to the present invention is continuously improved as a function of new scientific and truth data in order to expand to different crop types and to provide scaling to address practical needs of agriculture from sub-field to continental scales. The aforementioned SALUS crop model is a subset of a larger simulation engine within the crop simulation processor 153 which uses a combination of farmer reported data, government and academic statistics, and remote sensing to build a detailed scenario that describes genotypic conditions (i.e., crop parameters representing genotypic potentials of a crop), environmental conditions (i.e., weather, physical soil properties, and chemical soil properties), and management conditions (e.g., planting dates, fertilizer application dates and amounts, tillage date, depth, and material, etc.) of a growing crop. Based on these input conditions, the crop model calculates plant growth stage, plant leaf area, solar energy absorbed through the leaves, biomass accumulated in different plant tissues, and water and nutrient uptake by the roots, and saves outputs for that day. These variables are calculated at every time step until the crop matures.

Accordingly, the crop simulation processor 153 is configured to describe development and growth of a crop within an agricultural parcel all the way from planting to maturity. Plant development describes the timing of events that occur during the plant life cycle that induce changes in growth rates and partitioning of dry matter to different plant tissues. The crop simulation processor 153 calculates state variables representing various aspects of development and growth at each daily time step and furthermore describes the different components of the soil layers and how these interact with the environment. Thus, the crop simulation processor 153 may estimate the amount of water and nutrients available for uptake by a growing plant. Root development occurs at each daily time step: root tips progress through the soil layers, and root mass increases. This results in water and nutrient uptake in soil horizons that are in contact with the plant's rooting system, proportional to the root mass distribution in each soil horizon. Advantageously, the crop simulations performed by the crop simulation processor 153 reflect the complex interactions whereby soil and weather influence plant growth and how plant growth subsequently changes the soil dynamic. Outputs of the crop simulation processor 153 include, but are not limited to, yields, nitrogen stress, drought stress, biomass accumulation, growth stages, nitrogen uptake, nitrogen use efficiency, and water use efficiency.

In one embodiment, constraints, weights, and search parameters that a user may specify to access parcel records in the parcel database 151 include, but are not limited to, growing region, state, county, zip code, Public Land Survey System (PLSS), keywords, parcel owner name, historical land use (e.g., crop type), land type (e.g., farm, dairy, ranch, forest, etc.), parcel acreage, tillable area, regenerative management practices, and agricultural metrics and valuations generated by the CO2E sequestration server 130.

As will be described in further detail below, the agricultural metrics and valuations generated by the CO2E sequestration server 130 enable a user functioning in a specific role (e.g., farmer, enterprise, underwriter, etc.) to understand the regenerative potential along with the value of a particular parcel from the user's perspective, and to trust that implemented regenerative management practices indeed sequester the amount of carbon which was offered in carbon credits. Depending on the user's role, agricultural metrics may be expressed as productivity of a parcel, production risk of the parcel, and the parcel's potential to be sustainably managed under one or more regenerative management practices. For a user purely interested in farming, a parcel's productivity, stability (i.e., productivity risk), and regenerative sustainability are paramount. However, for an enterprise that is focused on reducing carbon emissions, the regenerative sustainability metric may take precedence. In one embodiment, the agricultural valuation assigned to a parcel employs one or more of the agricultural metrics as a function of the user's role as supplemented by comparable sales to express an agricultural value in dollars as opposed to just a value that is based on comparable parcels. Advantageously, the user is exposed to a valuation of a parcels based upon the parcel's agricultural potential, which is a substantial improvement over that which has heretofore been provided.

Figure 10:
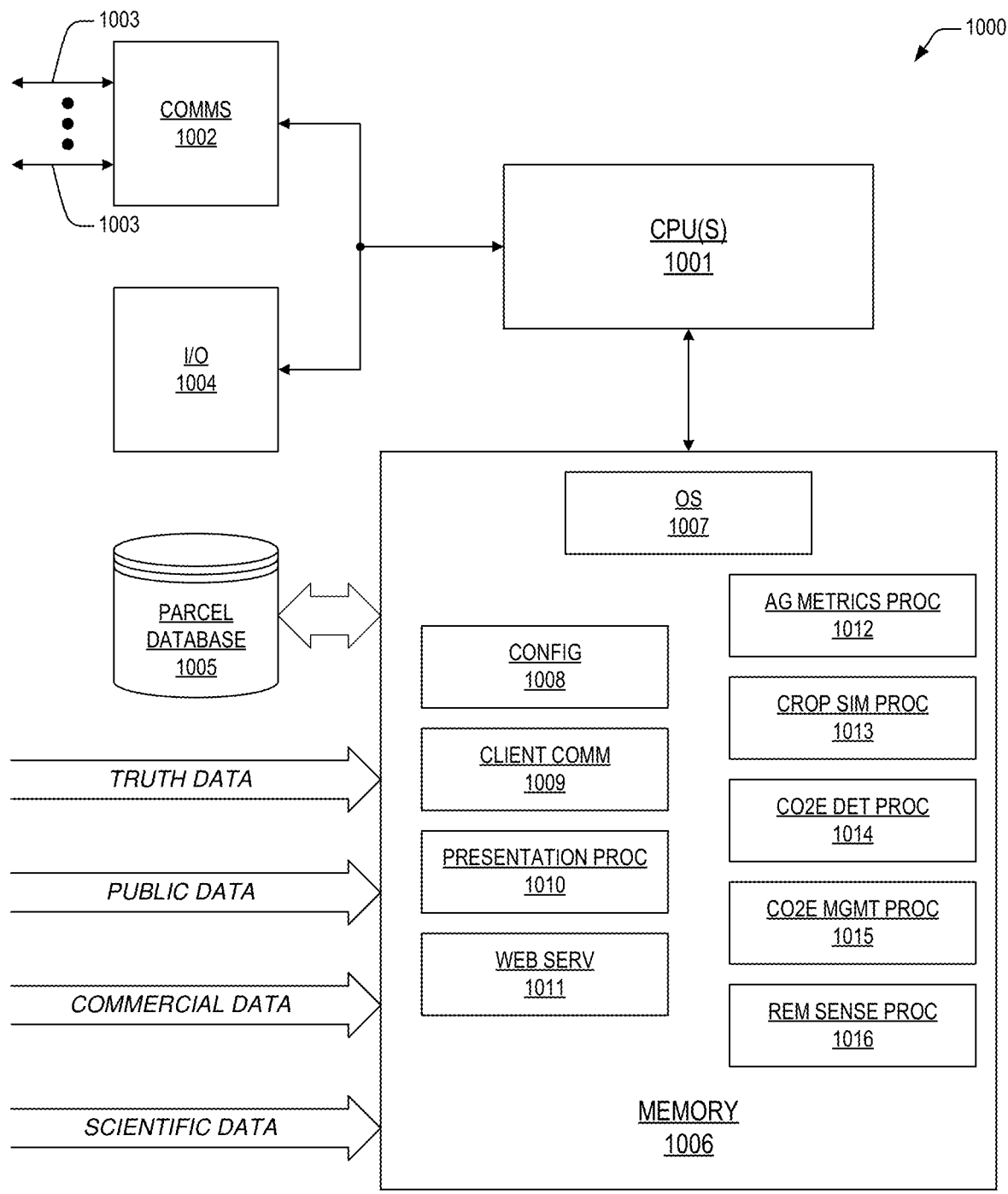
FIG. 10 is a block diagram illustrating a carbon sequestration server according to the present invention.

The CO2E sequestration server 130 according to the present invention may comprise one or more application programs executing thereon to perform the operations and functions described above, and which will be disclosed in further detail with reference to FIG. 10.

Figure 2:
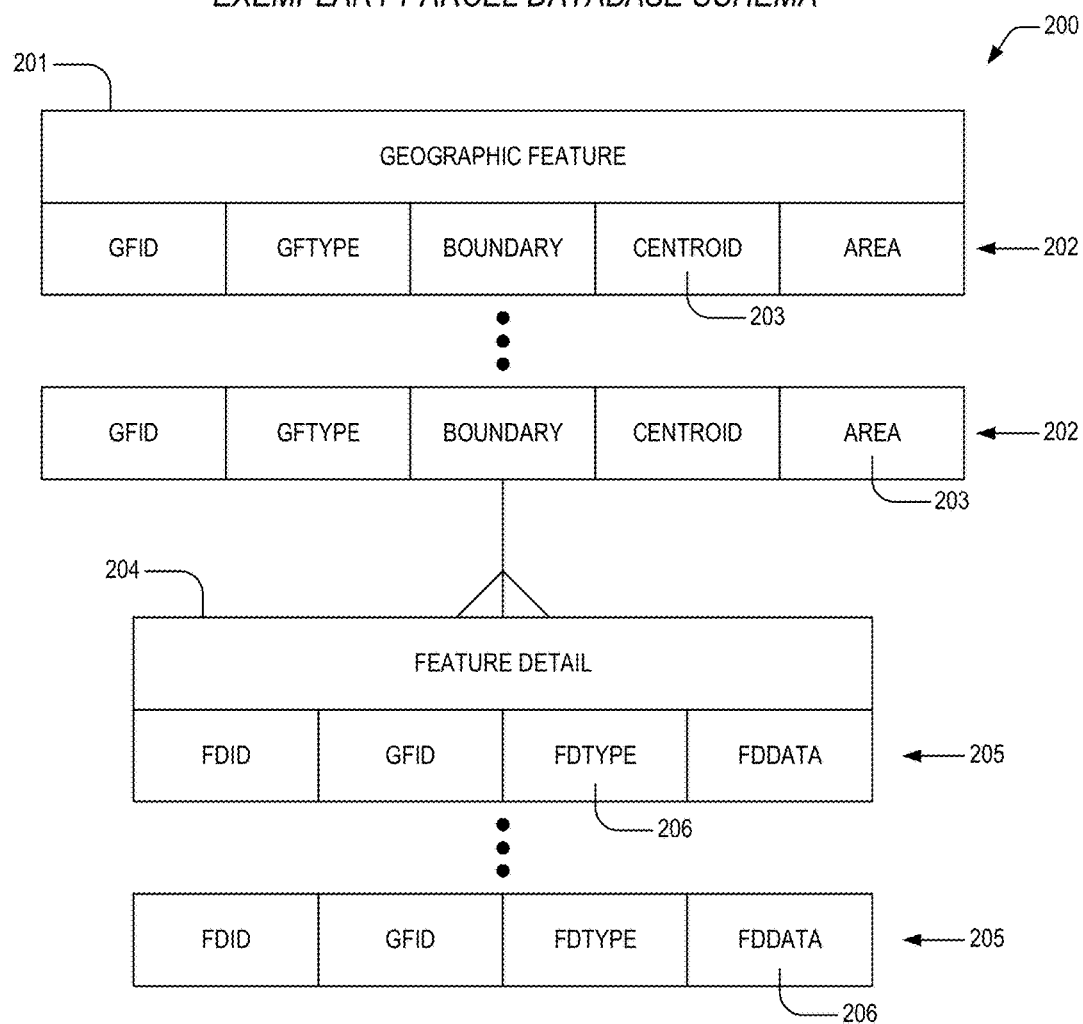
FIG. 2 is a block diagram depicting an exemplary schema for a parcel database according to the present invention.

Turning to FIG. 2, a block diagram is presented depicting an exemplary schema for a parcel database 200 according to the present invention, such as the parcel database 151 of FIG. 1. The schema 200 may include a geographic feature table 201 that is linked to a plurality of feature detail tables 204 in a one-to-many architecture. The geographic feature table 201 may include a plurality of records 202 having a plurality of data fields 203. Each of the feature detail tables 204 may include a plurality of records 205 having a plurality of data fields 206. The plurality of data fields 203 in each of the geographic feature records 202 include a geographic feature ID field (GFID), which is the primary key for the geographic feature table 201 and which is unique for each of the plurality of records 202. The plurality of data fields 203 in each of the geographic feature records 202 additionally include a geographic feature type field (GFTYPE), a boundary field (BOUNDARY), a centroid field (CENTROID), and an area field (AREA). GFTYPE specifies one of a plurality of geographic feature types that include, but are not limited to, parcel, county, state, and growing region. BOUNDARY includes geographic coordinates (e.g., longitude and latitude) that describe a geographic boundary for the land area corresponding to the GFID. CENTROID includes a geographic centroid coordinates for the land area corresponding to the GFID. And AREA includes the area (e.g., acres, square meters, etc.) of the land area corresponding to the GFID.

The plurality of data fields 206 in each of the feature detail records 205 include a feature detail ID field (FDID), which is the primary key for a corresponding feature detail table 204 and which is unique for each of the plurality of records 205. Each of the feature detail records 205 may also include a geographic feature type ID field (GFID), which is the foreign key that links a feature detail record 205 back to a corresponding geographic feature record 202 in the geographic feature table 201. Each of the feature detail records 205 may further include a feature detail type field (FDTYPE) and a feature detail data field (FDDATA). FDTYPE specifies one of a plurality of feature detail types that include, but are not limited to, results generated by the crop simulation processor 153 for the corresponding FDID and GFID combination, a particular agricultural metric (e.g., productivity score, stability score, regenerative potential score, agricultural valuation) generated by the agricultural metrics processor 152 for the corresponding FDID and GFID combination, stability zone boundaries generated by the remote sense processor 156 for the corresponding FDID and GFID combination, and descriptive metadata taken from the databases 121-124 for the corresponding FDID and GFID combination.

Accordingly, a given geographic feature (e.g., a 40-acre farm in Milford County, Iowa) may be described in the parcel database 151 in terms of its geographic boundary, centroid, and area within a record 202 in the geographic feature table 201, and this record 202 may be linked to a number of feature detail records 205 in different feature detail tables 204 that contain feature detail data for a corresponding number of feature detail types.

As one skilled in the art will appreciate, deciphering the history and potential of a parcel is critical to understanding the parcel's ultimate regenerative potential and economic value; however, this type of information is typically not available outside of hard-to-come-by operator data, and without access to this data, those interested in assigning CO2E sequestration potential and value to a parcel are typically limited to public soil maps and state-level productivity rankings, which are inadequate for representing actual field conditions. In addition, one skilled in the art will appreciate that most states don't have a consistent productivity score that allows for comparison of parcels across states, and that state productivity scores are based on historical information of weather and soil. In contrast, the metrics and valuations provided for by the present invention are 1) consistent and 2) based upon topography, soil, and crop simulations that are validated by remote sensing in test fields.

Figure 3:
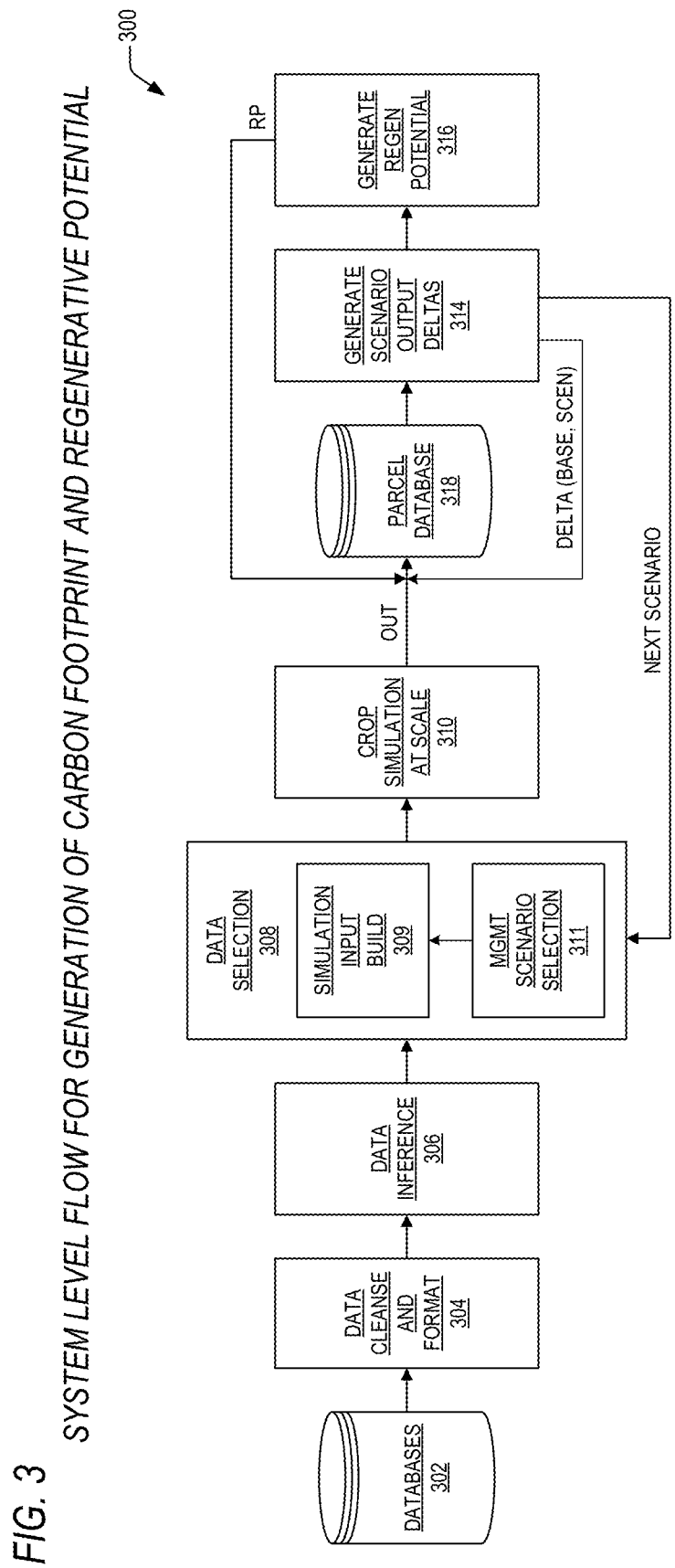
FIG. 3 is a block diagram featuring a system level flow for automated carbon footprint and regenerative potential determination associated with agricultural parcels within a prescribed growing region.

Now referring to FIG. 3, a flow diagram 300 is presented featuring system level flow for generation of carbon footprint potentials along with regenerative potential metrics associated with agricultural parcels within a prescribed growing region, such as might be performed by the CO2E sequestration server 130 of FIG. 1, and such as might be stored in the exemplary parcel database records 200 of FIG. 2. Flow begins at block 304 where databases 302 are accessed and data therefrom is automatically cleansed of error and formatted for analysis and simulation. In one embodiment, the databases 302 comprise databases 121-124 of FIG. 1. As one skilled in the art will appreciate, one of the most challenging issues associated with the processing of so-called "big data" is processing lots of data from different sources that are formatted differently, updated differently, and that contain different types of errors. Accordingly, the accessing, cleansing, and formatting data in block 304 may comprise a core set of steps for each data source, namely, downloading the data, assessing and cleansing the data, and formatting and storing the data.

The downloading step may comprise automating downloads for those data sources that require more frequent updates. For example, irrigation data may only have to be downloaded a few times per year, but weather data has to be downloaded daily. In addition, for data that is retroactively updated due to more accurate sources, the automation task may comprise downloading more recent days in the past, comparing their data to current downloads of those days, and continuing to update the data until it stabilizes.

The downloading step may additionally comprise automating ingestion of different data formats such as, but not limited to, CSV or Excel files, public database formats, scanned images, Power Point files, and PDF files.

Once downloaded, the data is assessed and cleansed, which may comprise removal of duplicate information, inferring missing values, substituting for unconventional characters and symbols, and removal of outlier values (e.g., tax assessment data having extra zeros). For data that will be ingested regularly, the present invention contemplates automation of assessment and cleansing. Inference of missing values may comprise employing alternative data (e.g., using state/national average management practices in situations where county records lack such data). It is noted that assessment and cleansing of satellite/aerial data is particularly challenging since clouds or other obstacles may obscure images. In one embodiment, the assessing and cleansing step comprises automated processes to filter out images with obscured data.

The formatting and storage of the data may include determination of whether data may be stored in a single file or may require a database or file store (e.g., Amazon Simple Storage Service). Preferably, small amounts of data are stored as files (e.g., county-level USDA data) and large amounts of data (e.g., weather data, satellite/aerial imagery, field trials data, and parcel metadata) are stored in databases which are accessed via a microservice architecture. One example of such is a service that accepts parcel boundaries to access soil zones for a given parcel. Another example is a service that accepts parcel boundaries to access the yearly weather for the given parcel.

At block 306, data that has been cleansed and formatted in block 304 is analyzed for each parcel to generate inferences regarding a number of attributes that include, but are not limited to, crop types, crop rotations and cover cropping, key management practices (e.g., planting dates; tillage types and dates; fertilization types, amounts, and dates; irrigation amounts and dates; buffer zones, drainage control, harvesting dates), and stages of crop growth at any given time. These inferences may be generated by the CO2E management processor 154 and the remote sense processor 156 of FIG. 1, and are provided to the data selection block 308. The CO2E management processor 154 is configured to make the above inferences because it is programmed with grower management practices that are common to different geographical areas. Accordingly, the CO2E management processor 154 applies this information to a particular field location in order to build a scenario of "typical farming" on that field. For example, given a field in central Illinois, the CO2E management processor 154 may provide the following information: "Farmers in this area typically plant a corn/soy rotation. The maturity group for corn is 110 RM, which would be planted around May 15. Farmers typically apply 150 pounds of nitrogen fertilizer in a split application: 100 pounds the day before planting, and 50 pounds as a mid-season side-dressing. The maturity group for soy is 3.8, which would be planted around May 21. No fertilizer would be applied for soy. Most farmers in this area use conventional tillage, but 10% of them use conservation tillage. Advantageously, the CO2E management processor 154 makes these inferences to generate simulation inputs to the crop simulation processor 153, which in turn may simulate typical results on a field even when nothing is known about the actual farmer's practices on that exact field. In addition, the CO2E management processor 154 allows simulation inputs to be built with imperfect information, namely, if some of the farmer's actual practices for the field are known, the CO2E management processor 154 is configured to provide realistic values for the management practices that are unknown.

The CO2E management processor 154 bases its inferences on USDA-reported practices, as well as scientific knowledge of how farmers make decisions. For example, the USDA might report that in a particular region fertilizer amounts vary from 120 to 170 pounds, but scientific data indicates that farmers apply more fertilizer to fields that have higher productivity. Accordingly, the CO2E management processor 154 employs this information to generate a more precise estimate of how much fertilizer would be used on a given field. As one skilled in the art will appreciate, the length of the growing season is different in different parts of the country. Plant breeders create different varieties of the same base plant (e.g., corn, soy, etc.) that are optimized for different growing seasons and these varieties mature at different rates. A corn cultivar may be described as "110 RM" where the "RM" stands for "relative maturity", and the 110 means that the plant takes about 110 days from germination to maturity. In Northern corn-growing regions such as North Dakota, the growing season is short, and farmers typically plant "short RM" varieties of corn, to ensure the corn matures before the onset of winter. In areas where the growing season is longer, farmers plant "longer RM" varieties of corn, which will take advantage of the longer growing season to produce a higher yield. Accordingly, the CO2E management processor 154 is configured to employ this information in making inferences about baseline practices on a field where management practices data is incomplete.

The remote sense processor 156 in conjunction with the CO2E detection processor 155 may make inferences associated with crop rotation, cover cropping, fertilizer application, and tillage, if sufficient image data is available. Absent sufficient image data, the CO2E management processor 154 may employ supplemental verification methods. For example, if there is insufficient image data available to verify a crop rotation using remote sensing, the CO2E management processor 154 may access the databases 302 to read, say, electronic planting records uploaded from a combine to infer that a specified crop rotation occurred. In another example, if there is insufficient image data available to verify nitrogen application (dates and amounts), the CO2E management processor 154 may access the databases 302 to read electronic records ("as applied" files produced by a combine as a real-time records of nitrogen fertilizer application that are timestamped and tagged to a specific geographical location) to infer that a specified amount of nitrogen was applied on a specified date.

At the data selection block 308, the generated parcel attributes along with other data necessary for simulation of crops corresponding to all of the parcels are selected on a parcel by parcel basis. A subset of data selection may comprise building a list of inputs to a crop simulation model within the crop simulation processor 153 of FIG. 1 that utilize management practices for a plurality of management scenarios. In one embodiment, the plurality of management scenarios may comprise a baseline management scenario (i.e., current management practices for a parcel) and a best regenerative practices scenario (i.e., regenerative management practices that maximize carbon sequestration over a period of growing seasons). In another embodiment, the plurality of management scenarios may comprise the baseline management scenario, the best regenerative practices scenario, and one or more better regenerative management practices scenarios (i.e., selected regenerative management practices that increase, but not maximize, carbon sequestration over a period of growing seasons). Another subset of data selection may comprise building a list of inputs to a crop simulation model within the crop simulation processor 153 of FIG. 1 that utilize management practices taken from one of the plurality of management scenarios. The process of building simulation inputs is shown in block 309 and may also comprise a set of directives that guide building of the simulation inputs according to management practices from each of the plurality of management scenarios for parcels within a given area. Preferably, the simulation inputs are built according to automated directives that rely solely on inferred data, without human intervention. In one embodiment, data selection provides for the combination of known and inferred data that includes management practices, soil data, and weather data (including long-term forecasts) according to the set of directives. From these directives, the data selection block 308 produces a complete input set for crop simulation. Flow then proceeds to block 310.

At block 310, the simulation inputs for all parcels within a prescribed region are provided to the crop simulation processor 153, which executes crop simulations for respective crops corresponding to each of the parcels over a period of years under each of the plurality of management scenarios, where the crops and number of years are provided by the simulation inputs. In one embodiment, the prescribed region may be the entire United States. In another embodiment, the prescribed region may be a specific growing region (e.g., the Corn Belt, the Wheat Belt). In a further embodiment, the prescribed region may comprise a given state (e.g., Iowa). In yet another embodiment, the prescribed region may comprise a county (e.g., Marshall County, IA). Though the prescribed regions are preferably associated within parcels within the United States, the present inventors note that the system 100 according to the present invention may be adapted for practice within any country in the world. Thus, according to the inputs provided by block 308, crop simulations are run at scale by the crop simulation processor 153 to generate components (e.g., CO2 flux from the soil, N20 flux from the soil, CO2 from tractor fuel use, CO2 from production of nitrogen fertilizer, etc.) from which greenhouse gas emissions in units of CO2E are calculated, parcel yields per planting season along with a number of other corresponding simulation outputs such as, but not limited to, plant growth stage, plant leaf area, solar energy absorbed through the leaves, biomass accumulated in different plant tissues, and water and nutrient uptake by the roots. In one embodiment, crop growth is simulated daily and outputs for each day are saved and employed as parameters for the next growing day. These variables are calculated at every time step until a crop for each parcel matures. In one embodiment, the crop simulation processor 153 is configured to perform millions of crop simulations in hours and is configured to run simulations for corn, soybeans, cotton, or wheat on any agricultural location in the U.S. The simulation results are stored in the parcel database 318. Flow then proceeds to block 314.

At block 314, the CO2E determination processor 155 determines CO2E sequestration for each of the parcels by calculating greenhouse gas emissions under the baseline management scenario from emissions corresponding to one of the plurality of regenerative practices scenarios (e.g., best practices or better practices scenarios) and converting these emissions into units of CO2E. Accordingly, the value of CO2E sequestration reflects the amount of CO2E that can be sequestered in the soil by implementing one or more regenerative management practices over baseline management practices. The CO2E sequestration values are stored in the parcel database 318 along with their corresponding management practices scenarios. Flow then proceeds to block 316.

At block 316, the agro-economic metrics processor 152 accesses the database 318 and employs the simulation results to generate a plurality of agro-economic metrics for every parcel in the parcel database 318, which include a regenerative potential metric for each of the parcels. Some of the plurality of metrics, as will be described in further detail below, may exclusively employ simulation outputs while others of the metrics may employ simulation outputs in combination with data retrieved from the databases 302. Some of the metrics may not require simulation outputs, but rather may utilize satellite/aerial image data. Some of the metrics may be iteratively generated as is shown in the diagram 300, while other metrics may be directly generated. In one embodiment the following agro-economic metrics are generated at block 316:

a productivity score for each parcel that is expressed as a value from 0 to 100 relative to all other parcels within a prescribed region;

a stability (or, "field reliability") score for each parcel that is expressed as a value from 0 to 100 relative to all other parcels within a prescribed region; and a regenerative potential score for each parcel that is expressed as a value from 0 to 100 relative to all other parcels within a prescribed region.

The productivity score is a measure of the ability of a particular parcel to support crop production under common management practices in its historical environment. In this context, productivity is the outcome of interactions among the main components of a crop production system that impact crop performance, namely weather, soil, and management practices. The stability score is a measure of the risk associated with producing crops on the particular parcel of land over a range of years. The regenerative potential score is a measure of a parcel's ability to sustainably grow crops over a range of years under best regenerative management practices. The agro-economic metrics processor 152 may further access the aforenoted metrics along with data from the databases 302 to calculate an agricultural value for each of the parcels that considers the relative scoring of the agricultural metrics as supplemented by comparable sales of surrounding parcels. In one embodiment, as will be described in further detail below, the productivity score for each parcel is employed in conjunction with productivity scores for surrounding parcels along with USDA census and sales data to generate an objective valuation of each parcel that is expressed in dollars per acre. Other embodiments contemplate employment of other and/or additional agricultural metrics to arrive at an agricultural valuation that is meaningful to a given user's role (e.g., farmer, enterprise farm, banking, underwriting). Further embodiments envision the employment of weighted agricultural metrics to generate an agricultural valuation that is meaningful to a given user's role. The agricultural metrics along with the agricultural valuation(s) for each of the parcels are then stored in the parcel database 318 along with other parcel data as is described above with reference to FIGS. 1-2.

Figure 4:
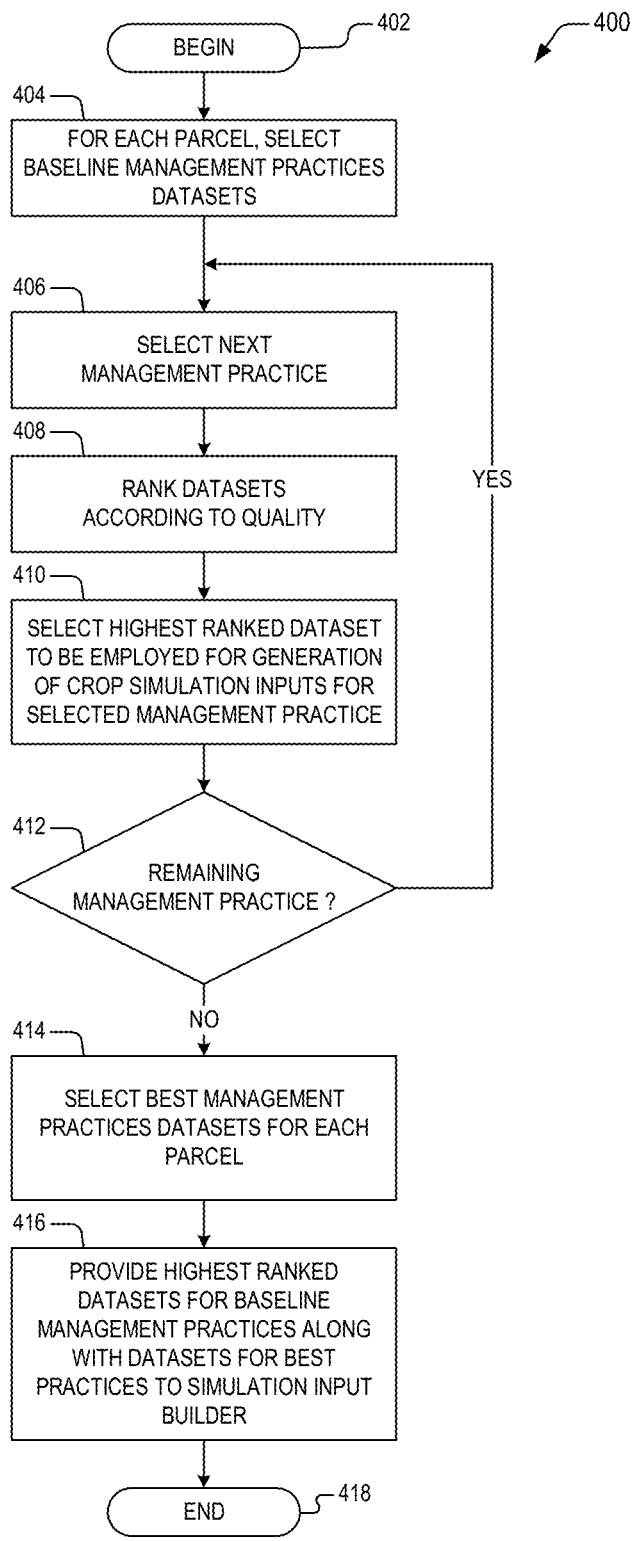
FIG. 4 is a flow diagram illustrating processing and ranking of management practices associated with baseline and best practices for generation of inputs to a crop simulation processor according to the present invention.

Now turning to FIG. 4, a flow diagram 400 is presented illustrating processing and ranking of management practices associated with baseline and best practices for generation of inputs to a crop simulation processor according to the present invention. As alluded to above, the CO2E management processor 154 may access the outputs of the remote sense processor 156 to evaluate and rank the outputs against other management practice data that is received from one or more of the databases 121-124 and from the CO2E detection processor 155. In turn, the CO2E management processor 154 may augment sparse or incomplete data in order to provide location-specific inferences for key crop management practices including, but not limited to, planted crop type, specific cultivar or crop variety, planting data, planting density (i.e., row spacing), dates and amounts of fertilizer application, and irrigation practices. Flow begins at block 402, where it is directed to build simulation inputs for both baseline management practices and best regenerative management practices in order to determine CO2E sequestration amounts for each of the parcels in the parcel database 151. Flow then proceeds to block 404.

At block 404, all baseline management practices datasets are selected for each of the parcels. As one skilled in the art will appreciate, management practice data and corresponding datasets are highly dependent on location and type of management practice. For some practices and locations, a trusted dataset may be available, but which is incomplete along with a less-trusted, but complete dataset. In addition, available datasets may be more or less geographically granular ranging from state averages, to county averages, all the way down to data based on 30-meter grid. Finally, some management practices also may rely on a heuristic devised by agronomists. For example, a common rule of thumb for determining how much fertilizer a farmer would typically use is based on the expected amount of yield for a given crop. Flow then proceeds to block 406.

At block 406, a next baseline management practice is selected and flow proceeds to block 408.

At block 408, all of the baseline datasets for the selected baseline management practice are evaluated and ranked according to quality. This ranking is performed by automated directives that rank the baseline datasets according to their ability to generate inputs to the crop simulation processor 153 to produce outputs that are accurate when compared to field trials and scientific data. Flow then proceeds to block 410.

At block 410, for the selected baseline management practice, the highest ranked baseline management practice dataset is selected for generation of crop simulation inputs. Flow then proceeds to decision block 412.

At decision block 412, an evaluation is made to determine if there are any remaining baseline management practices whose datasets have not been assessed, ranked, and selected for generation of crop simulation inputs. The present inventors note that the selected value for one management practice may affect the selection of another. For instance, if corn is selected as a crop, then the planting date must be a date which is suitable for planting corn at a given location. A different crop selection would result in a different planting date selection. Accordingly, the CO2E management processor 154 develops automated directives that take into account dependency ordering of different management practices. If there are remaining baseline management practices, then flow proceeds to block 406. If not, then flow proceeds to block 414

At block 414, best regenerative management practices datasets are selected for each of the parcels in the parcel database 151. Flow then proceeds to block 416.

At block 416, the highest ranked baseline management practices dataset corresponding to each management practice along with the best regenerative management practices dataset are provided to a simulation input builder that generates inputs for the crop simulation processor 153 for both baseline management practices and best regenerative management practices. Flow then proceeds to block 418.

At block 418, the method completes.

The present inventors note that though the diagram 400 illustrates selection of management practices for both baseline and best regenerative management scenarios, the flow may be adapted to include one or more better regenerative management scenarios, as are described above.

Figure 5:
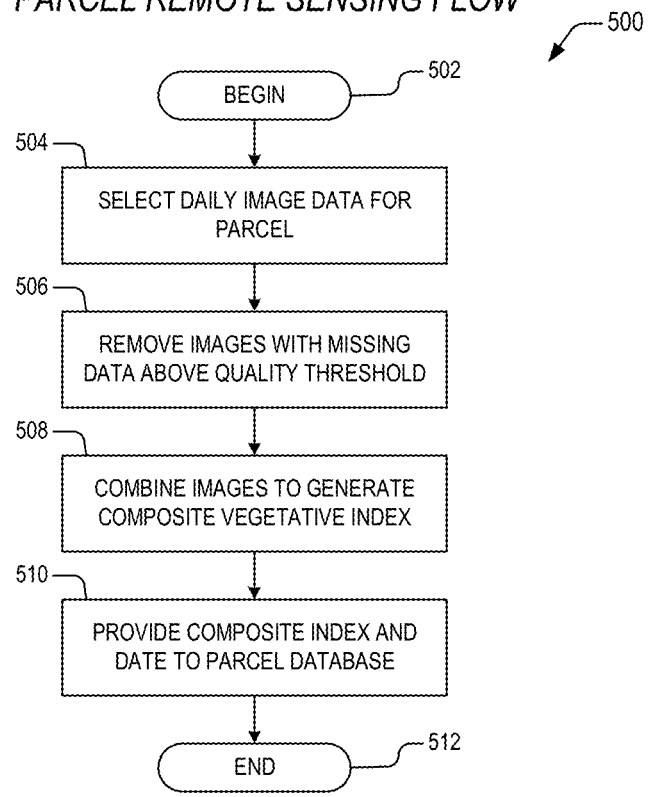
FIG. 5 is a flow diagram showing automated processing of remote sensed data for determination, monitoring, and verification of carbon sequestration within a parcel.

Referring now to FIG. 5 is a flow diagram 500 is presented showing automated processing of remote sensed data for determination, monitoring, and verification of carbon sequestration within a parcel, such as may be performed by the remote sense processor 156 of FIG. 1. In one embodiment, the remote sense processor 156 processes satellite and/or aerial images to determine implementation and maintenance of one or more regenerative management practices for parcels for which carbon credits and corresponding grower incentives have been reserved. As noted above, these practices include, but are not limited to, crop type, specific cultivar or crop variety, planting data, planting density (i.e., seeds per acre and row spacing), tillage types and dates, fertilizer application (e.g., types, dates, and amounts), crop rotation and cover cropping, irrigation (e.g., dates and amounts), buffer zoning, and drainage control. The remote sense processor 156 may process satellite and/or aerial images at frequencies commensurate with monitoring and implementation and maintenance of the aforenoted one or more regenerative management practices. Flow begins at block 502, where it is directed to process satellite and/or aerial images on a date that is selected to confirm implementation and maintenance of selected ones of the one or more regenerative management practices. Flow then proceeds to block 504

At block 504, the remote sense processor 156 accesses public and/or commercial data to determine implementation and maintenance of selected ones of the one or more regenerative management practices. Image data may be from the public database 122 or the commercial database 123. As described above, the images are downloaded, assessed and cleansed, and stored. Flow then proceeds to block 506.

At block 506, images that have missing data (e.g., covered by clouds) above a prescribed quality threshold are removed and images with missing data below the prescribed quality threshold are retained. Some of the missing data in the retained images may be estimated by time-processing data from other time-adjacent images which include that data. Flow then proceeds to block 508.

At block 508, relevant spectral bands for a given observation are combined to generate composite vegetative indices for subparts of the parcels according to well-known techniques. Preferably, the Landsat Surface Reflectance-derived Enhanced Vegetation Index (EVI) is employed to determine crop type and maturity. Another embodiment contemplates use of the normalized difference vegetation index (NDVI) for purposes of determining crop type and maturity. In one embodiment, red, green, blue, near-infrared, and short-wave infrared spectral bands are combined to generate composite vegetative indices. For tillage, the remote sense processor 156 is configured to distinguish different tillage types as a function of the amount of residue on present on a field for, as one skilled in the art will appreciate, different amounts of residue present on the field result in different near-IR signatures. Accordingly, the remote sense processor 156 may employ one or more residue indices such as, but not limited to, Normalized Difference Tillage Index (NDTI), Shortwave Infrared Normalized Difference Residue Index (SINDRI), and Cellulose Absorption Index (CAI) to distinguish tillage practices in a manner substantially similar to the employment of EVI and other spectral indices to determine crop type and maturity. Flow then proceeds to block 510.

At block 510, the remote sense processor 156 identifies a best vegetative index image for each of the parcels for the prescribed date and provides this data to the parcel database 151. Flow then proceeds to block 512.

At block 512, the method completes.

Figure 6:
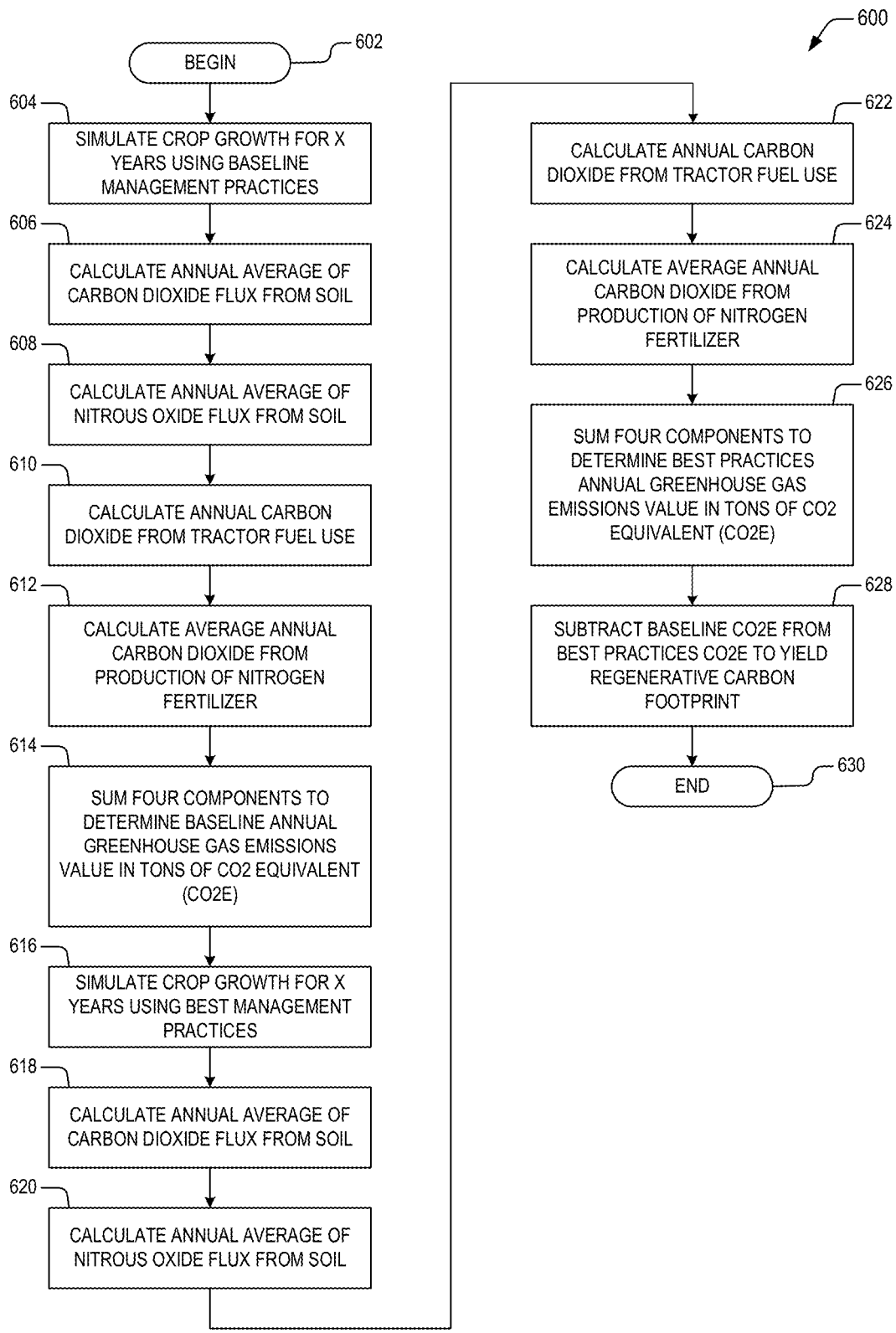
FIG. 6 is a flow diagram illustrating a method for automatically determining regenerative carbon footprint using best practices for an agricultural parcel.

Turning now to FIG. 6 is a flow diagram illustrating a method for automatically determining a regenerative carbon footprint using best practices for an agricultural parcel. Flow begins at block 602, where inputs for baseline management practices scenarios and best regenerative management practices scenarios generated by the management practices scenario builder flow 400 of FIG. 4 are provided by the CO2E management processor 154 to the crop simulation processor 153. Flow then proceeds to block 604.

At block 604, simulations are executed by the crop simulation processor 153 under the baseline management practices scenario for a specified number (X) of years to generate outputs that include components that may be employed to accurately simulate greenhouse gas emissions for each parcel. In one embodiment, the specified number (X) of years comprises 10 years. Another embodiment contemplates the specified number (X) equal to five years. Outputs for each of the X years are stored within the parcel database 151. Flow then proceeds to block 606.

At block 606, the CO2E determination processor 155 retrieves outputs corresponding to carbon dioxide flux from the soil (one component of the greenhouse gas emissions for each parcel) from the parcel database 151 and calculates the carbon dioxide flux from the soil by taking the difference in total soil organic carbon between the ends of the first year and last year simulations, and dividing the difference by the total number of years minus one. The result is the average change in soil per year over all years except the first. The total soil organic carbon is computed as the sum of three outputs of the crop simulation processor 153: belowground active organic carbon (C_ActOrgBl), belowground slow organic carbon (C_SloOrgBl), and belowground resistant organic carbon (C_ResOrgBl). The CO2E determination processor 155 then converts the total soil organic carbon value into total soil organic carbon dioxide. Flow then proceeds to block 608.

At block 608, the CO2E determination processor 155 retrieves outputs corresponding to nitrous oxide flux from the soil (a second component of the greenhouse gas emissions for each parcel) from the parcel database 151 and calculates the nitrous oxide flux from the soil by multiplying the amount of nitrogen fertilizer applied by a standard conversion factor, which is converted to nitrous oxide and then to carbon dioxide equivalents. In one embodiment, conversion values from the United Nations Intergovernmental Panel on Climate Change (IPCC) put forth in IPCC 2014, which are:

$$CO_2-N_2O_{SOIL}=N_{FERTILIZER}*0.0125*(44/28)*265.$$

This value is calculated for each simulation year and the mean is taken as an average annual CO2E component. Flow then proceeds to block 610.

At block 610, the CO2E determination processor 155 retrieves outputs corresponding to carbon dioxide from tractor fuel use (a third component of the greenhouse gas emissions for each parcel, which represents the annual carbon dioxide released to the atmosphere when tractors use fossil fuels during planting, cultivation, harvest, etc.) from the parcel database 151 and calculates this component based on formula published in McSwiney, C. P., Bohm, S., Grace, P. R. and Robertson, G. P. (2010), *Greenhouse Gas Emissions Calculator for Grain and Biofuel Farming Systems*. Journal of Natural Resources and Life Sciences Education, 39: 125-131. doi:10.4195/jnrlse.2009.0021. Specifically, the amount of diesel per hectare used by a tractor is multiplied by the amount of carbon dioxide released when burning diesel (from the U.S. Energy Information Administration) and this is multiplied by conversion constants. The formula is:

$$CO_{2\text{-}FUEL}=(47 \text{ liters diesel/ha})*(22.4 \text{ lb } CO_2/\text{gal diesel})*K$$

where K represents conversions between kilograms and pounds and between liters and gallons.

This value is calculated once, as it is the same for each year of the baseline management practices scenario. Flow then proceeds to block 612.

At block 612, the CO2E determination processor 155 retrieves outputs corresponding to carbon dioxide from the production of nitrogen fertilizer (a fourth component of the greenhouse gas emissions for each parcel, which represents carbon dioxide emissions resulting from the production of nitrogen fertilizer) from the parcel database 151 and calculates this fourth component by multiplying the annual amount of nitrogen fertilizer applied to the parcel by a conversion factor published in: Robertson G P, Paul E A, Harwood R R. *Greenhouse gases in intensive agriculture: contributions of individual gases to the radiative forcing of the atmosphere*. Science. 2000 Sep. 15; 289 (5486): 1922-5. doi: 10.1126/science.289.5486.1922. PMID: 10988070. The formula employed is:

$$CO_{2\text{-}FERTILIZER\text{-}PRODUCTION} = N_{FERTILIZER} * 4.51.$$

This value is calculated for each simulation year and the mean is taken as an average annual CO2E component. Flow then proceeds to block 614.

At block 614, the four greenhouse gas emissions components generated at blocks 606, 608, 610, and 612 are summed together to yield the annual carbon dioxide emissions for the parcels due under the baseline management practices scenario. Flow then proceeds to block 616.

At block 616, simulations are executed by the crop simulation processor 153 under best regenerative management practices for a specified number (X) of years to generate outputs that include components that may be employed to accurately simulate greenhouse gas emissions for each parcel under the best regenerative management practices scenario. In one embodiment, the specified number (X) of years comprises 10 years. Another embodiment contemplates the specified number (X) equal to five years. Outputs for each of the X years are stored within the parcel database 151. Flow then proceeds to block 618.

At block 618, the CO2E determination processor 155 retrieves outputs corresponding to carbon dioxide flux from the soil (the first component of the greenhouse gas emissions for each parcel) from the parcel database 151 and calculates the carbon dioxide flux from the soil under the best regenerative management practices scenario in the same manner as under the baseline management practices scenario described with reference to block 606. Flow then proceeds to block 620.

At block 620, the CO2E determination processor 155 retrieves outputs corresponding to nitrous oxide flux from the soil (the second component of the greenhouse gas emissions for each parcel) from the parcel database 151 and calculates the nitrous oxide flux from the soil under the best regenerative management practices scenario in the same manner as under the baseline management practices scenario described with reference to block 608. Flow then proceeds to block 622.

At block 622, the CO2E determination processor 155 retrieves outputs corresponding to carbon dioxide from tractor fuel use (the third component of the greenhouse gas emissions for each parcel) from the parcel database 151 and calculates the carbon dioxide from tractor fuel use under the best regenerative management practices scenario in the same manner as under the baseline management practices scenario described with reference to block 610. Flow then proceeds to block 624.

At block 624, the CO2E determination processor 155 retrieves outputs corresponding to carbon dioxide from the production of nitrogen fertilizer (the fourth component of the greenhouse gas emissions for each parcel) from the parcel database 151 and calculates the carbon dioxide from tractor fuel use under the best regenerative management practices scenario in the same manner as under the baseline management practices scenario described with reference to block 612. Flow then proceeds to block 626.

At block 626, the four greenhouse gas emissions components generated at blocks 618, 620, 622, and 624 are summed together to yield the annual carbon dioxide emissions for the parcels under the best regenerative management practices scenario. Flow then proceeds to block 628.

At block 628 the annual carbon dioxide emissions under the baseline management practices scenario determined at block 614 are subtracted from the annual carbon dioxide emissions under the best management practices scenario to yield each parcel's regenerative carbon footprint potential value, which is stored in the parcel database 151. Flow then proceeds to block 630.

At block 630, the method completes.

The present inventors note that though the parcel carbon footprint determination flow of FIG. 6 illustrates the maximum amount of sequestration that can be achieved when implementing all best regenerative management practices, the present invention also contemplates determination of a parcel's carbon footprint potential under selected ones of the best regenerative management practices.

Figure 7:
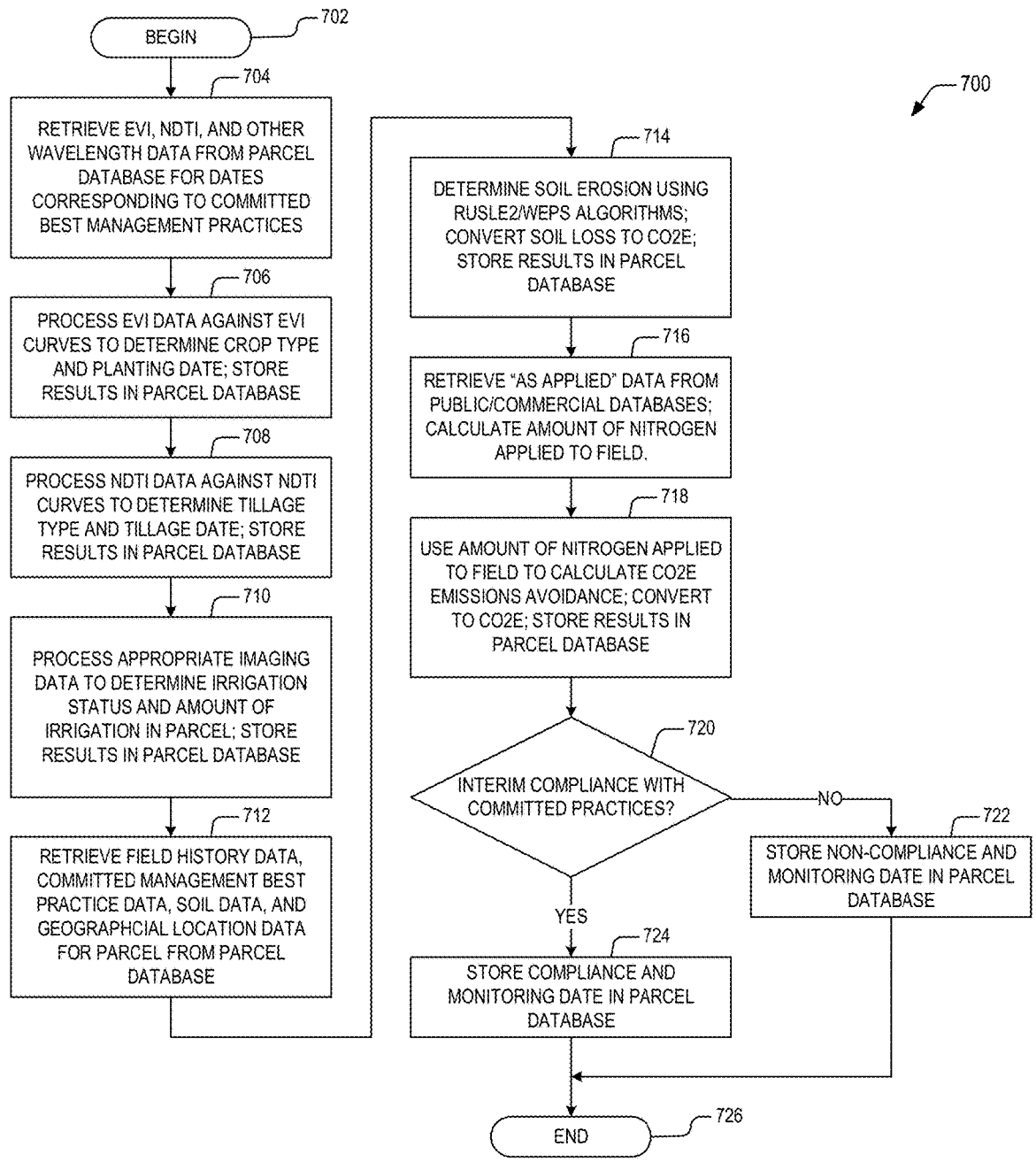
FIG. 7 is a flow diagram detailing a method for automatically monitoring a grower's implementation of regenerative management practices according to the present invention.

Referring to FIG. 7 is a flow diagram 700 is presented detailing a method for automatically monitoring a grower's implementation of regenerative practices according to the present invention. Flow begins at block 702 where it is determined to monitor implementation of one or more best regenerative management practices committed to by a grower. In one embodiment, the grower may have elected to implement the one or more best regenerative management practices in exchange for an incentive payment from a carbon credit broker. It is the purpose of the parcel CO2E sequestration monitoring flow of FIG. 7 to provide an automated technique to monitor progressive implementation of the one or more best regenerative management practices by the grower over the course of a growing season in order to provide confirmation to purchasers of corresponding carbon credits that the value of greenhouse gas emissions associated with the carbon credits has indeed been reduced through implementation of the one or more best regenerative management practices by the grower. Flow then proceeds to block 704.

At block 704, the CO2E determination processor 155 retrieves EVI data for the parcel that corresponds to implementation of the one or more best regenerative management practices. Flow then proceeds to block 706.

At block 706, the CO2E determination processor 155 processes the retrieved EVI data against EVI maturity curves to determine crop type, planting date, and maturity. The CO2E determination processor 155 is configured to infer what crop is growing in a particular field, and when that crop emerged from the ground. This is done by monitoring a vegetative index (such as EVI or NDVI) over time. Different crops have different vegetative index curves, so by observing the increases in EVI/NDVI over time, the CO2E determination processor 155 can infer what crop is growing and when the crop was planted. Flow then proceeds to block 708.

At block 708, the CO2E determination processor 155 is configured to infer tillage practices on a field, such as tillage type and tillage date. This is done by monitoring an index (e.g., NDTI) over a period of time. Different tillage practices lead to different amounts of residue on the field surface, so by observing the changes in NDTI over time the CO2E determination processor 155 can infer which tillage practices have been employed and when corresponding tillage events occurred. For example, as one skilled in the art will appreciate, a tillage event will cause an abrupt change in NDTI values, and this abrupt change is employed by the CO2E determination processor 155 to detect a tillage event and to infer timing of the event. Flow then proceeds to block 710.

At block 710, the CO2E determination processor 155 is configured to infer irrigation practices, such as irrigation status and amount of irrigation. To determine irrigation practices, the CO2E determination processor 155 may employ a machine-learning algorithm that recognizes the characteristic shapes of irrigated fields, which are distinctly different from the characteristic shapes of non-irrigated fields. This is done by monitoring visual image data such as, but not limited to, Sentinel and Landsat images Fields that are irrigated have a different appearance from fields that are not irrigated, and irrigated fields differ in appearance based upon how much water is applied (e.g., irrigated portions of a field will be greener than unirrigated portions, and the difference between the two will be proportional to the amount of irrigation water applied). In one embodiment, the CO2E determination processor 155 employs an index based on wavelengths to detect moisture content of leaf surfaces. In this embodiment, the CO2E determination processor 155 may employ a convolutional neural network to identify irrigated fields using the wavelength-based index. In addition, the CO2E determination processor 155 is configured to detect the colors of irrigated and non-irrigated fields and process the differences in color to infer the amount of irrigation water that has been applied over time. In one embodiment, the CO2E determination processor 155 comprises linear model based on ground truth data accessed from the truth database 121, where the linear model is configured to infer irrigation types, dates, and amounts as a function of related color differences in the images. Accordingly, the appropriate wavelengths from the irrigated fields are compared to the same wavelengths on unirrigated fields, and the differences in intensity of wavelengths between the irrigated and unirrigated fields are converted to differences in water applied to the irrigated fields. Preferably, the CO2E determination processor 155 may utilize Normalized Difference Water Index (NDWI) images to infer the irrigate ion types, dates, and amounts. As one skilled in the art will appreciate, NDWI images are based on near infrared (NIR) and short-ware infrared (SWIR) wavelengths since reflection intensity is largely a function of the presence of chlorophyll, resulting in commensurate increases/decreases in the absorption of light by water. High absorption is indicated in the SWIR regions and because water does not absorb NIR, this part of the spectrum may be also employed to render NDWI indices resistant to atmospheric effects. Results are stored in the parcel database 151. Flow then proceeds to block 712.

At block 712, the CO2E determination processor 155 retrieves from the parcel database 151 field history data, committed best management practice data, soil data, and geographical location data for the parcel. Flow then proceeds to block 714.

At block 714, the CO2E determination processor 155 processes the field history data, committed best management practice data, soil data, and geographical location data retrieved at block 712 to determine weight of soil erosion over a prescribed period of time corresponding to implementation of the regenerative management practices. As one skilled in the art will appreciate, a number of regenerative management practices (e.g., cover cropping, reduced tillage, etc.) result in reductions in soil erosion. In one embodiment, soil erosion is determined using the well-known Revised Universal Soil Loss Equation 2 (RUSLE2) algorithm, an overview of which is provided by the USDA at https://www.ars.usda.gov/southeast-area/oxford-ms/national-sedimentation-laboratory/watershed-physical-processes-research/research/rusle2/revised-universal-soil-loss-equation-2-overview-of-rusle2/. In another embodiment, soil erosion is determined using the well-known Wind Erosion Prediction System (WEPS) that is detailed by the USDA at https://www.nrcs.usda.gov/wps/portal/nrcs/main/national/technical/tools/weps/. Another embodiment contemplates employment of both RUSLE2 and WEPS for determination of soil erosion weight. Once the amount of soil erosion is determined, the CO2E determination processor 155 converts the weight of soil loss to CO2E as a function of the amount of carbon present in a soil type that corresponds to the parcel. The soil loss CO2E is then stored in the parcel database 151. Flow then proceeds to block 716.

At block 716, the CO2E determination processor 155 may retrieve "as applied" fertilizer data from the truth database 121 and may calculate the amount of nitrogen applied to the field. As one skilled in the art will appreciate, "as applied" data specifies the dates, types, and amounts of fertilizer that were applied to each portion of a parcel. Flow then proceeds to block 718.

Different types of fertilizers contain different amounts of nitrogen. From a public/commercial database, one can look up a conversion factor. So, by applying the correct conversion factor and adding up the amounts applied in different parts of the field, we can calculate the total amount of nitrogen applied to the field, as well as the amount applied to each part of the field.

At block 718, the amount of nitrogen applied to the field is employed to calculate a CO2 emissions avoidance value and the CO2 emissions avoidance value is converted to a CO2E value, which is stored in the parcel database 151. In one embodiment, calculation of the CO2 emissions avoidance value and conversion to a CO2E value is performed according to the IPCC guidelines for national greenhouse gas inventories. Flow then proceeds to decision block 720.

At decision block 720, an evaluation is made to determine if the processed regenerative practice data processed in blocks 704-718 for associated dates reflects ongoing compliance with implementation of the one or more best regenerative management practices. If so, then flow proceeds to block 724. If not, then flow proceeds to block 722.

At block 722, indications of appropriate practice non-compliance are stored in the parcel database along with the date of non-compliance. Knowing that from time to time a grower's implementation of regenerative practices may vary from was originally committed to. Accordingly, in one embodiment, the CO2E determination processor 155 may generate recalculation control signals that direct the CO2E sequestration system 100 to recalculate previously calculated carbon credits and incentives for the parcel based upon non-compliance and may also generate value change control signals to inform both the carbon credit purchaser and the grower of respective changes in valuation. In one embodiment, the value change control signals may comprise messages transmitted over one or more of the wired or wireless links 1003 to one or more of the client devices 101-103, where the client applications 104-106 executing thereon may function to decrease of valuations that correspond to payments for the carbon credits and incentive payment. Flow then proceeds to block 726.

At block 724, indications of appropriate practice compliance are stored in the parcel database along with the date of compliance. Flow then proceeds to block 716.

At block 726, the method completes.

The present inventors note that though soil loss through erosion, as described with reference to block 714 is not present in the method of FIG. 6 for determining carbon footprints under both baseline and regenerative management practices, the method may easily be modified to incorporate this additional contributor to a parcel's overall carbon footprint.

Figure 8:
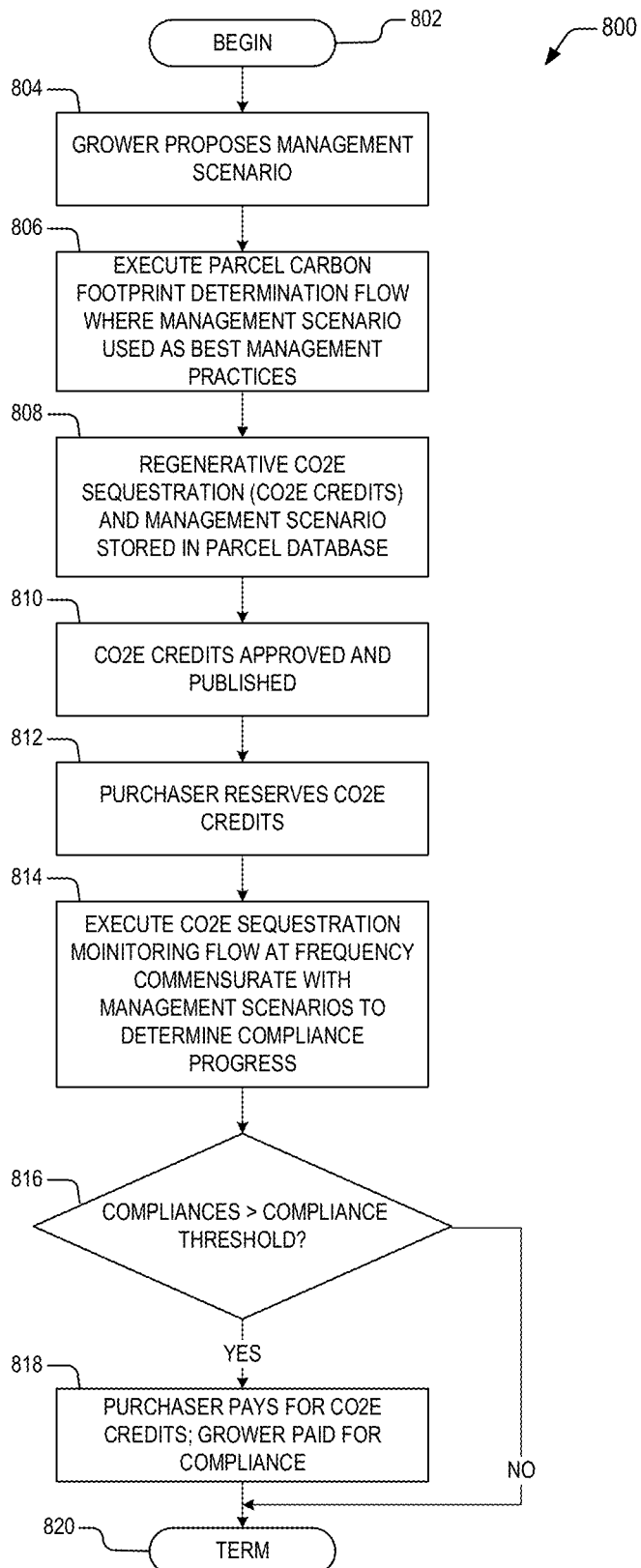
FIG. 8 is a flow diagram depicting a method for automatically verifying a grower's implementation of regenerative management practices according to the present invention.

Turning to FIG. 8, a flow diagram 800 is presented depicting a method for automatically verifying a grower's implementation of regenerative practices according to the present invention. Flow begins at block 802, where a grower is solicited to implement regenerative management practices via displays in one of the client devices 101-103. Flow then proceeds to block 804.

At block 804, from one of the client devices 101-103 the grower may propose a regenerative management practices scenario to implement one or more regenerative management practices in exchange incentive, which may be in the form of financial payments or credits. Flow then proceeds to block 806.

At block 806, the CO2E sequestration server 130 executes the carbon footprint determination flow of FIG. 6 to determine that carbon sequestration potential for the parcel due resulting from implementation of the regenerative management practices scenario of block 804 over the grower's baseline management practices scenario. Flow then proceeds to block 808.

At block 808, the carbon sequestration potential for the parcel and proposed regenerative management practices scenario are stored in the parcel database 151, and may be converted to carbon credits as described above. Flow then proceeds to block 810.

At block 810, the regenerative management practices carbon credits for the parcel are approved and published, and are accessed via one or more of the client devices 101-103.

At block 812, the stored carbon credits for the parcel may be reserved by a purchaser via one or more of the client devices 101-103. Flow then proceeds to block 814.

At block 814, the CO2E sequestration server 130 executes the parcel CO2E monitoring flow of FIG. 7 at a frequency commensurate with implementation and maintenance of the regenerative management scenario proposed at block 804. As described with reference to FIG. 7, compliances and non-compliances along with corresponding dates are stored in the parcel database. Flow then proceeds to decision block 816.

At decision block 816, at the end of a season (or incentive period) an evaluation is made by the CO2E determination processor 155 to verify that the grower indeed sequestered the amount of greenhouse gas emissions corresponding to reserved/purchased carbon credits through implementation and maintenance of the proposed regenerative management scenario. In one embodiment, the stored compliances and non-compliances are accessed and, for each of regenerative management practice that was proposed, an evaluation is made to determine if the number of compliances for the practice is greater than a prescribed compliance number threshold amount, where the prescribed compliance number threshold amount is set to verify with 90 percent certainty that the agreed upon regenerative management practice was implemented and maintained, thus providing verification to the purchaser. If the compliance threshold is met, then flow proceeds to block 818. If the compliance threshold is not met, then flow proceeds to block 820.

At block 818, the CO2E sequestration system 100 may generate first signals that direct the purchaser to pay for the carbon credits, and may generate second control signals that cause payment of the agreed upon incentive for implementing the regenerative management scenario to the grower. In one embodiment, the first and second signals may comprise messages transmitted over one or more of the wired or wireless links 1003 to one or more of the client devices 101-103, where the client applications 104-106 executing thereon may function to complete transfer of funds corresponding to payments for the carbon credits and incentive payment. In one embodiment, transfer of funds may be accomplished in conjunction with third-party payment processing systems and/or third-party carbon credit brokerage systems. Flow then proceeds to block 820.

At block 820, the method completes.

Advantageously, the CO2E sequestration system 100 according to the present invention provides a closed loop mechanism for automatically determining the amount of greenhouse gas emissions that may be sequestered for a parcel under implantation of a proposed regenerative management scenario, for automatically monitoring implementation and maintenance of the regenerative management scenario by a grower, and for providing verification to both grower and carbon credit purchaser that the amount of greenhouse gas emissions corresponding to purchased carbon credits has indeed been sequestered.

Figure 9:
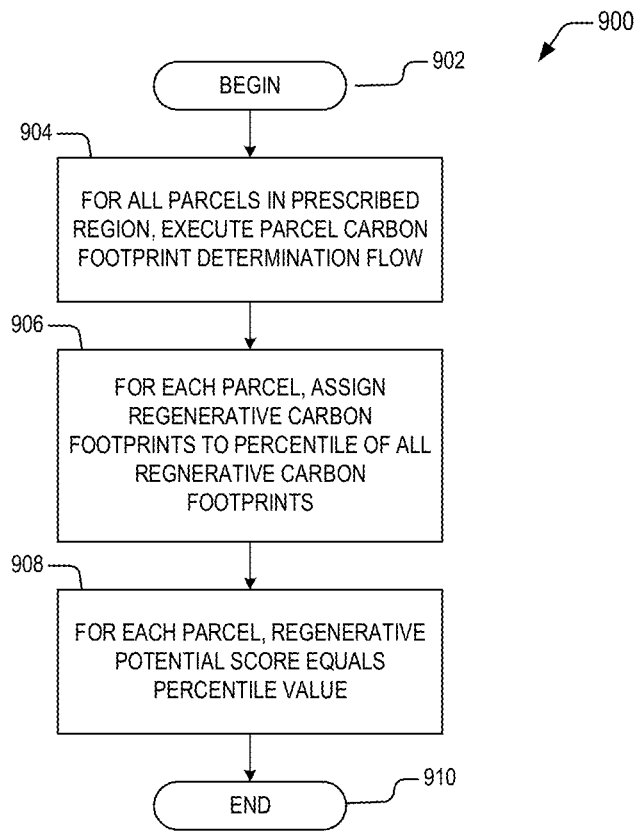
FIG. 9 is a flow diagram detailing a method for translation of carbon footprint associated with implementation of best regenerative management practices into a regenerative potential metric for an agricultural parcel relative to all other parcels within a specified growing region.

Now referring to FIG. 9, a flow diagram 900 is presented detailing an exemplary method for translation of determined best practices carbon footprint into a regenerative potential metric for an agricultural parcel relative to all other parcels within a specified growing region. As noted above, the regenerative potential metric, along with other metrics (e.g., productivity, production stability) generated by the CO2E sequestration server 130 and available for search an display on the client devices 101-103 enable a user to make meaningful comparisons of parcels withing an given region (e.g., township, county, state, growing region, etc.) as a function of a user's role as opposed to just a dollar per acre value that is based on comparable parcels. Advantageously, the user is exposed to a metric that expresses the valuation of a parcel based upon the parcel's regenerative potential, which is a substantial improvement over that which has heretofore been provided. The user may be a farmer responsible for cultivation of one or more parcels, where the regenerative potential metric provides for a technique to assign a value (financial or otherwise) to implementation of one or more regenerative management practices. The user may be a carbon credit broker responsible for buying and selling carbon credits within the carbon offset marketplace, where the regenerative potential metric provides for a technique to assign a market value to implementation of one or more regenerative management practices. The user may further be a purchaser of carbon credits, where the regenerative potential metric provides for a technique to determine if a carbon credit broker's valuation implementation of one or more regenerative management practices is in fair relative to the other parcels within the specified growing region.

Flow begins at block 902, where it is determined to generate regenerative potential metrics for all parcels within a prescribed region. Flow then proceeds to block 904.

At block 904, the CO2E sequestration server 130 executes the parcel carbon footprint determination flow 600 of FIG. 6 for all parcels within the prescribed region. Flow then proceeds to block 906.

At block 906, each parcel's regenerative carbon footprint determined at block 904 are assigned to a percentile bin relative to all other regenerative carbon footprint values corresponding to remaining parcels in the prescribed region. In one embodiment, the percentile bins range from 0 (i.e., implying no regenerative potential) to 100 (i.e., implying more regenerative potential than all other parcels in the prescribed region) in increments of one percent. Other embodiments contemplate binning in increments of five percent and 10 percent. Flow then proceeds to block 908.

At block 908, all of the parcel's regenerative potential scores are set to be equal to the percentile bins into which they were assigned at block 906. Accordingly, a parcel with a regenerative potential metric of, say, 90 has the potential to reduce greenhouse gas emissions though implementation of best regenerative practices twice as effectively over a parcel with a regenerative potential metric of 45. Flow then proceeds to block 910.

At block 910, the method completes.

Now tuning to FIG. 10 is a block diagram illustrating a carbon sequestration server according to the present invention, such as the server 130 of FIG. 1. The CO2E sequestration server 1000 may include one or more central processing units (CPU) 1001 that are coupled to memory 1006 having both transitory and non-transitory memory components therein. The CPU 1001 is also coupled to a communications circuit 1002 that couples the CO2E sequestration server 1000 to the internet cloud 110 via one or more wired and/or wireless links 1003. The links 1003 may include, but are not limited to, Ethernet, cable, fiber optic, and digital subscriber line (DSL). As part of the network path to and through the cloud 110, providers of internet connectivity (e.g., ISPs) may employ wireless technologies from point to point as well.

The CO2E sequestration server 1000 may also comprise input/output circuits 1004 that include, but are not limited to, data entry and display devices (e.g., keyboards, monitors, touchpads, etc.). The memory 1006 may be coupled to a parcel database 1005 and to the databases 121-124 described with reference to FIG. 1 above. Though the CO2E sequestration server 1000 is shown directly coupled to databases 121-124 and 1005, the present inventors note that interfaces to these data sources may exclusively be through the communications circuit 1002 or may be through a combination of direct interface and through the communications circuit 1002, according to the source of data.

The memory 1006 may include an operating system 1007 such as, but not limited to, Microsoft Windows, Mac OS, Unix, and Linux, where the operating system 1007 is configured to manage execution by the CPU 1001 of program instructions that are components of one or more application programs. In one embodiment, a single application program comprises a plurality of code segments 1008-1016 resident in the memory 1006 and which are identified as a configuration code segment CONFIG 1008, a client communications code segment CLIENT COMM 1009, a presentation processor code segment PRESENTATION PROC 1010, a web services code segment WEB SERV 1011, an agricultural metrics processor code segment AG METRICS PROC 1012, a crop simulation processor code segment CROP SIM PROC 1013, a CO2E determination processor code segment CO2E DET PROC 1014, a CO2E management practices processor code segment CO2E MGMT PROC 1015, and a remote sense processor code segment REM SENSE PROC 1016.

Operationally, the CO2E sequestration server 1000 may execute one or more of the code segments 1008-1016 under control of the OS 1007 as required to enable the CO2E sequestration server 1000 to ingest new data from external data sources 121-124, to employ data from the sources 121-124 in crop simulations that translate the data into values of CO2E that may be sequestered under one or more best management practices along with regenerative potential and other meaningful agricultural metrics and corresponding valuations for approximately 20 million agricultural parcels, and to store these values, metrics, and valuations in the parcel database 1005 in a manner that can be rapidly and easily searched and accessed by users that communicate with the CO2E sequestration server 1000 over the communications circuit 1002 via client applications 104-106 executing on their respective client devices 101-103. The CO2E sequestration server 1000 may further be configured to execute one or more of the code segments 1008-1016 under control of the OS 1007 as required to enable the CO2E sequestration server 1000 to format and present search results and corresponding parcel data to the client applications 104-106 executing on their respective client devices 101-103 and to receive communications therefrom that users specify to narrow search results or to perform new searches altogether.

CONFIG 1008 may be executed to place the server 1000 into an operational or maintenance mode, where the maintenance mode may be entered to allow for ingestion of new data from the data sources 121-124 via automated or manual means. CLIENT COMM 1009 may be executed to perfect reliable transfer of information between the CO2E sequestration server 1000 and client applications 104-106 executing on respective client devices 101-103. PRESENTATION PROC 1010 may be executed to perform searches of the parcel database 1005, to provide search results, and to interact with client applications 104-106 executing on respective client devices 101-103 as is described above with reference to FIGS. 1-3. WEB SERV 1011 may be executed to provide for formatting of information provided by PRESENTATION PROC 1010 for transmission to the client applications 104-106 and for formatting of information that is provided to PRESENTATION PROC 1010 which has been received from the client applications 104-106.

AG METRICS PROC 1012 may be executed to perform any of the functions and operations described above with reference to the agricultural metrics processor 152 of FIG. 1. CROP SIM PROC 1013 may be executed to perform any of the functions and operations described above with reference to the crop simulation processor 153 of FIG. 1. CO2E DET PROC 1014 may be executed to perform any of the functions and operations described above with reference to the CO2E determination processor 155 of FIG. 1. CO2E MGMT PROC 1015 may be executed to perform any of the functions and operations described above with reference to the CO2E management practices processor 154 of FIG. 1. REM SENSE PROC 1016 may be executed to perform any of the functions and operations described above with reference to the remote sense processor 156 of FIG. 1.

Figure 11:
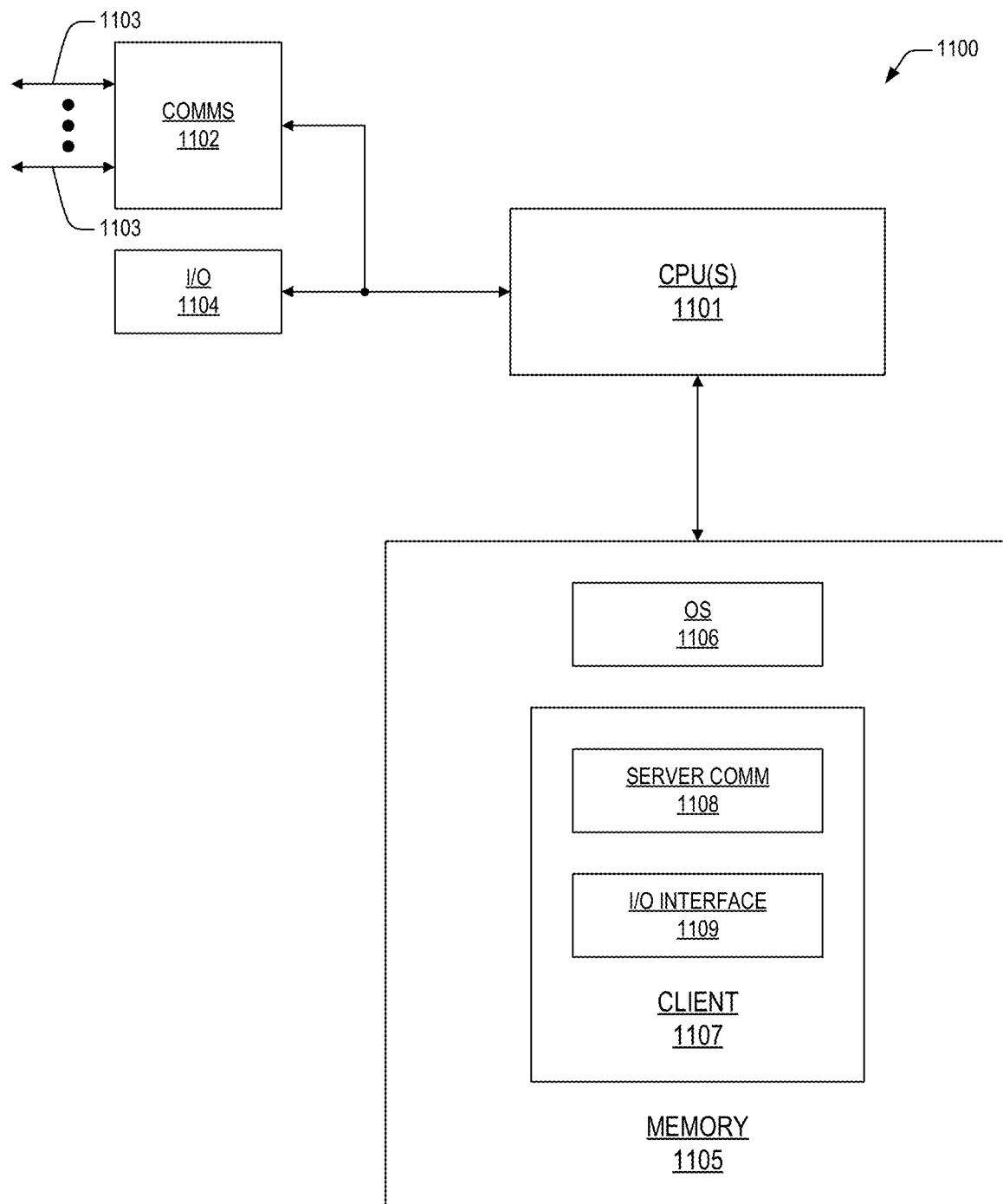
FIG. 11 is a block diagram depicting a client device according to the present invention.

Referring now to FIG. 11 is a block diagram depicting a client device according to the present invention, Now referring to FIG. 11, a block diagram is presented depicting a client device 1100 according to the present invention, such as the client devices 101-103 discussed above with reference to FIG. 1. The client device 1100 may include one or more central processing units (CPU) 1101 that are coupled to memory 1105 having both transitory and non-transitory memory components therein. The CPU 1101 is also coupled to a communications circuit 1102 that couples the client device 1100 to internet cloud 110 via one or more wired and/or wireless links 1103. The links 1103 may include, but are not limited to, Ethernet, cable, fiber optic, and digital subscriber line (DSL).

The client device 1100 may also comprise input/output circuits 1104 that include, but are not limited to, data entry and display devices (e.g., keyboards, monitors, touch pads, etc.).

The memory 1105 may include an operating system 1106 such as, but not limited to, Microsoft Windows, Mac OS, Unix, Linux, iOS, and Android OS, where the operating system 1106 is configured to manage execution by the CPU 1101 of program instructions that are components of a client application program 1107. In one embodiment, the client application program 1107 comprises a server communications code segment SERVER COMM 1108 and an I/O interface code segment I/O INTERFACE 1109.

When executing on the client device 1100, the client application program 1107 provides for display of information provided by the CO2E sequestration server 130, 1000 on the input/output circuits 1104 that help a user make decisions regarding which parameters to specify in order to perform searches of the parcel database 151, 1005. The SERVER COMM 1108 segment may execute to receive this information and the I/O INTERFACE segment 1109 may execute to transmit this information to the input/output circuit 1104. Likewise, the client 1107 provides for input of search parameters provided by the user via the input/output circuit for transmission to the CO2E sequestration server 130, 1000 that direct the CO2E sequestration server 130, 1000 to refine an ongoing search in order to narrow down a number of parcels that satisfy the search parameters or to specify parameters that direct the CO2E sequestration server 130, 1000 to perform new searches altogether. The SERVER COMM 1108 segment may execute to transmit this information and the I/O INTERFACE segment 1109 may execute to receive this information to the input/output circuit 1104.

The functions and operations described above with reference to the CO2E sequestration server 130, 1000 according to the present invention result in a significant improvement in this field of technology by providing a superior technique for translating massive amounts of agricultural data for millions of parcels into potentials of the parcels to sequester carbon under one or more regenerative management practices and to provide agriculturally meaningful metrics and corresponding agricultural valuations and that aggregate the metrics and valuation along with public and commercial sales data for these parcels into detailed parcel reports that are displayed on client devices 101-103, 1100. In one embodiment, data corresponding to the detailed parcel reports are stored in the parcel database 151 for all agricultural parcel in the United States, approximately 20 million parcels. The parcel report is the culmination all of the functions and operations described above and includes a combination of data from public datasets, commercial datasets, management practices inference, remote sensing inference, crop simulation results, and final metric and agricultural algorithmic results. In one embodiment, to enable a search interface for users, the CO2E sequestration server 130, 1000 indexes key pieces of the data within the parcel database 151 into a full-text search engine. This allows users to filter through millions of parcels to retrieve those which fit their particular search criteria with sub-second search response time. Exemplary client device displays will now be presented with reference to FIGS. 12-16 that show how exemplary data is presented to a user, how exemplary search parameters are input by the user for transmission to the CO2E sequestration server 130, 1000, and how information is displayed to the user via exemplary detailed parcel reports.

Figure 12:
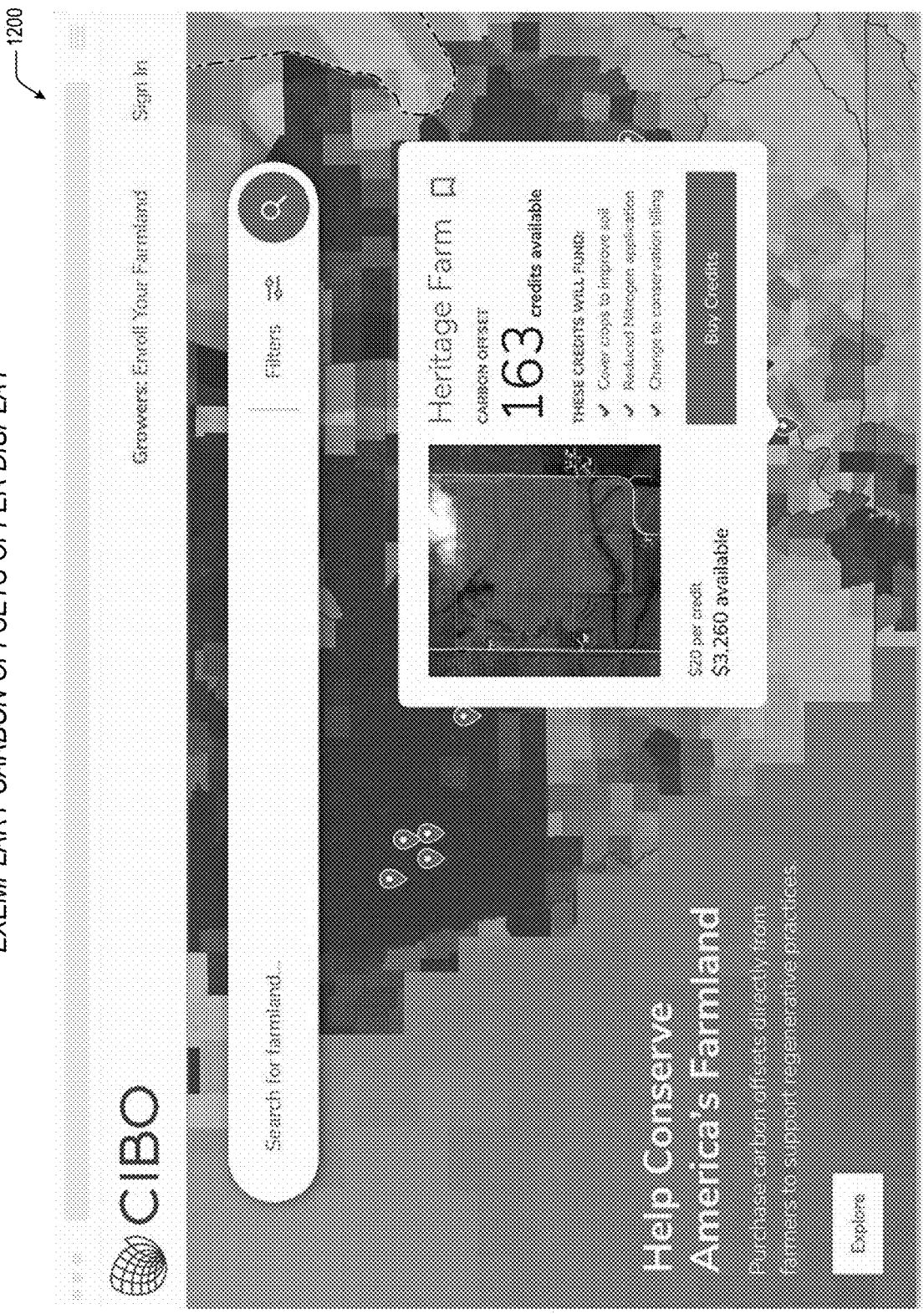
FIG. 12 is a diagram featuring an exemplary carbon offsets offer display according to the present invention such as might be presented by the client device of FIG. 11.

Turning now to FIG. 12 is a diagram featuring an exemplary carbon offsets offer display 1200 according to the present invention such as might be presented by the client device 1100 of FIG. 11. The display 1200 includes a freeform entry field, wherein a user may enter growing region, state, county, zip code, Public Land Survey System (PLSS), keywords, parcel owner name, historical land use (e.g., crop type), land type (e.g., farm, dairy, ranch, forest, etc.), parcel acreage, tillable area, regenerative potential score, and other agricultural metrics and agricultural valuations generated by the CO2E sequestration server 130, 1000. The display also features a parcel, Heritage Farm, for which 163 carbon offset credits are available at a price of $20 per credit. The credits are available for purchase via activating a "Buy Credits" button. As noted above, the CO2E sequestration server 130, 1000 has determined an amount of greenhouse gas sequestration for the Heritage Farm under the following regenerative management practices:

Cover crops to improve soil;
Reduced nitrogen fertilizer application; and
Changeover to conservation tillage practice.

Implicit in this offer are incentives that have been proffered to the parcel owner to implement and maintain the above regenerative management practices.

Figure 13:
FIG. 13 is a diagram showing an exemplary detailed carbon footprint comparison display according to the present invention such as might be presented by the client device of FIG. 11.

Referring to FIG. 13, a diagram is presented showing an exemplary detailed carbon footprint comparison display 1300 according to the present invention such as might be presented by the client device 1100 of FIG. 1. In addition to a terrain map locating a parcel (Field 43), the display 1300 shows a baseline management practices total carbon footprint for the parcel of 1,112 pounds of CO2E along with values of the four component employed by the CO2E sequestration server 130, 1000 to generate the footprint. The display 1300 also shows a regenerative management practices total carbon footprint for the parcel of 949 pounds of CO2E along with values of the four component employed by the CO2E sequestration server 130, 1000 to generate the footprint. The display 1300 further lists the regenerative management practices to which the parcel owner has been incentivized to implement. The display 1300 finally shows 20-year average yields for both baseline and regenerative management practices for both corn and soy.

Turning to FIG. 14, a diagram is present3ed illustrating an exemplary parcel regenerative potential display 1400 according to the present invention such as might be presented by the client device 1100 of FIG. 11. The display 1400 is in the format of a land regeneration report that depicts a timeline of greenhouse gas emission reductions over a 3-year period if corn/soy rotation practices are implemented. The display 1400 depicts each of the four components of the parcel's carbon footprint that are output from crop simulations performed by the CO2E sequestration server 130, 1000 under baseline and regenerative practices.

Now referring to FIG. 15, a diagram is presented detailing an exemplary carbon sequestration progress display 1500 according to the present invention such as might be presented by the client device 1100 of FIG. 11. As monitored through remote sensing, display 1500 indicates that the CO2E sequestration server 130, 1000 has verified on June 12 that the grower indeed planted soy on May 1 and that a $212.34 incentive was paid on July 3. The display 1500 also indicates that the grower committed to plant cover crops on November 15 and that monitoring of this practice implementation is to take place on January 15. The display 1500 further shows a progress bar for implementation of the two regenerative management practices along with the amount of carbon reduction to date.

Now turning to FIG. 16, a diagram is presented detailing an exemplary parcel search results display 1600 according to the present invention such as might be presented by the client device 1100 of FIG. 11. In the right side of the display 1600, a list of parcels that meet search parameters that the user entered in the mid portion of the display 1600. The parcels are ranked and displayed based upon how closely they meet the criteria entered by the user in the mid portion of the display 1600. The right portion of the display 1600 is scrollable as parcels are sorted from highest rank to lowest rank. The left portion of the display 1600 shows an average carbon footprint of 3,814 parcels in Bremer County, Iowa of 344 pounds CO2E per acre per year along with a cost of $210 per acre cost to enroll. The mid portion of the display 1600 comprises a freeform search field as described above, sliders that enables a user to specify a range of regenerative potential scores, tillable area, productivity scores, and field reliability (stability) scores for search. The display 1600 further shows check boxes whereby the user may specify different types of crops and rotations along with baseline and regenerative management practices.

Portions of the present invention and corresponding detailed description are presented in terms of software or algorithms, and symbolic representations of operations on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" or "displaying" or the like, refer to the action and processes of a computer system, a microprocessor, a central processing unit, or similar electronic computing device, that manipulates and transforms data represented as physical, electronic quantities within the computer system's registers and memories into other data similarly represented as physical quantities within the computer system memories or registers or other such information storage, transmission or display devices.

Note also that the software implemented aspects of the invention are typically encoded on some form of program storage medium or implemented over some type of transmission medium. The program storage medium may be electronic (e.g., read only memory, flash read only memory, electrically programmable read only memory), random access memory magnetic (e.g., a floppy disk or a hard drive) or optical (e.g., a compact disk read only memory, or "CD ROM"), and may be read only or random access. Similarly, the transmission medium may be metal traces, twisted wire pairs, coaxial cable, optical fiber, or some other suitable transmission medium known to the art. The invention is not limited by these aspects of any given implementation.

The particular embodiments disclosed above are illustrative only, and those skilled in the art will appreciate that they can readily use the disclosed conception and specific embodiments as a basis for designing or modifying other structures for carrying out the same purposes of the present invention, and that various changes, substitutions and alterations can be made herein without departing from the scope of the invention as set forth by the appended claims. For example, components/elements of the systems and/or apparatuses may be integrated or separated. In addition, the operation of the systems and apparatuses disclosed herein may be performed by more, fewer, or other components and the methods described may include more, fewer, or other steps. Additionally, unless otherwise specified steps may be performed in any suitable order.

Although specific advantages have been enumerated above, various embodiments may include some, none, or all of the enumerated advantages.

What is claimed is:

1. A method for monitoring implementation and maintenance of regenerative management practices in agricultural parcels, the method comprising:

via a server:
first determining baseline management practices for a first agricultural parcel;
first simulating crop growth for the first agricultural parcel for a prescribed number of growing seasons using said baseline management practices;
first computing first average yearly greenhouse gas emissions components from first outputs of said first simulating crop growth and first aggregating the first average yearly greenhouse gas emissions components to yield baseline annual carbon dioxide equivalent emissions;
second determining regenerative management practices for the first agricultural parcel, wherein the regenerative management practices comprise regenerative tillage practices to improve carbon sequestration;
second simulating crop growth for the first agricultural parcel for the prescribed number of growing seasons using said regenerative management practices;
second computing second average yearly greenhouse gas emissions components from second outputs of said second simulating crop growth and second aggregating the second average yearly greenhouse gas emissions components to yield regenerative annual carbon dioxide equivalent emissions; and
subtracting the baseline annual carbon dioxide equivalent emissions from the regenerative annual carbon dioxide equivalent emissions to yield a first regenerative carbon footprint for the first agricultural parcel;

via communications circuits disposed in a client device:
transmitting acceptance of an offer to the server to implement the offered regenerative management practices for the first agricultural parcel; and via the server:
employing remote sensing at a corresponding frequency to infer implementation of the regenerative management practices, said employing comprising:
via a processor disposed within the server:
removing images having missing data above a prescribed quality threshold;

retaining images having missing data below the prescribed quality threshold;

processing images not missing data that are time-adjacent to the retained images having missing data by estimating the missing data of the retained images having missing data using the images not missing data that are time-adjacent; and for a given image of images not missing data and the retained images having missing data that was estimated, combining relevant spectral bands of the given image to generate composite vegetative indices for subparts of the first agricultural parcel; and determining that the inferred implementation of the regenerative management practices is compliant with the offered regenerative management practices of the offer;

in response to determining that the inferred implementation of the regenerative management practices is compliant with the offered regenerative management practices of the offer:

transmitting an indication of compliance to a purchaser of carbon credits; and transmitting signals that cause payment of an incentive corresponding to the offer for implementing the regenerative management practices.

2. The method as recited in claim 1, wherein the regenerative management practices further comprise rotation of crops to improve carbon sequestration, and wherein Enhanced Vegetation Index (EVI) images and crop curves are processed and evaluated to determine compliance/noncompliance with crop types and planting dates.

3. The method as recited in claim 1, wherein Normalized Different Tillage Index (NDTI) images and crop curves are processed and evaluated to determine compliance/noncompliance with tillage types and tillage dates.

4. The method as recited in claim 1, further comprising:

for key dates corresponding to implementation and maintenance of a regenerative irrigation practice that comprises one of the regenerative management practices, processing and evaluating remotely sensed visual images against wavelength-based indexes to determine compliance/noncompliance indicators that correspond to each of the key dates.

5. The method as recited in claim 4, wherein said processing and evaluating remotely sensed visual images against wavelength-based indexes comprises:

detecting colors corresponding to irrigated and non-irrigated fields within a prescribed region corresponding to the parcel, and inferring an amount of irrigation applied to the parcel based upon intensities of the remotely sensed visual images compared to the wavelength-based indices.

6. The method as recited in claim 1, wherein greenhouse gas emissions for both the baseline and regenerative carbon footprints are calculated by simulating crop growth for 10 years to determine baseline average yearly greenhouse gas emissions and regenerative average yearly greenhouse gas emissions.

7. The method as recited in claim 6, wherein components of the baseline and regenerative average yearly greenhouse gas emissions comprise average carbon dioxide flux from the soil, nitrous oxide flux from the soil, carbon dioxide from tractor fuel use, and carbon dioxide from production of nitrogen fertilizer.

8. A non-transitory computer-readable storage medium storing program instructions that, when executed by a computer, cause the computer to perform a method for monitoring implementation and maintenance of regenerative management practices in agricultural parcels, the method comprising:

via a server:

first determining baseline management practices for a first agricultural parcel;

first simulating crop growth for the first agricultural parcel for a prescribed number of growing seasons using said baseline management practices;

first computing first average yearly greenhouse gas emissions components from first outputs of said first simulating crop growth and first aggregating the f first average yearly greenhouse gas emissions components to yield baseline annual carbon dioxide equivalent emissions;

second determining regenerative management practices for the first agricultural parcel, wherein the regenerative management practices comprise regenerative tillage practices to improve carbon sequestration;

second simulating crop growth for the first agricultural parcel for the prescribed number of growing seasons using said regenerative management practices;

second computing second average yearly greenhouse gas emissions components from second outputs of said second simulating crop growth and second aggregating the second average yearly greenhouse gas emissions components to yield regenerative annual carbon dioxide equivalent emissions; and subtracting the baseline annual carbon dioxide equivalent emissions from the regenerative annual carbon dioxide equivalent emissions to yield a first regenerative carbon footprint for the first agricultural parcel;

via communications circuits disposed in a client device:

transmitting acceptance of an offer to the server to implement offered regenerative management practices for the first agricultural parcel; and via the server:

employing remote sensing at a corresponding frequency to infer implementation of the regenerative management practices, said employing comprising:

via a processor disposed within the server:

removing images having missing data above a prescribed quality threshold;

retaining images having missing data below the prescribed quality threshold;

processing images not missing data that are time-adjacent to the retained images having missing data by estimating the missing data of the retained images having missing data using the images not missing data that are time-adjacent; and for a given image of images not missing data and the retained images having missing data that was estimated, combining relevant spectral bands of the given image to generate composite vegetative indices for subparts of the first agricultural parcel; and determining that the inferred implementation of the regenerative management practices is compliant with the offered regenerative management practices of the offer;

in response to determining that the inferred implementation of the regenerative management practices is compliant with the offered regenerative management practices of the offer:
transmitting an indication of compliance to a purchaser of carbon credits; and
transmitting signals that cause payment of an incentive corresponding to the offer for implementing the regenerative management practices.

9. The non-transitory computer-readable storage medium as recited in claim 8, wherein the regenerative management practices comprise rotation of crops to improve carbon sequestration, and wherein Enhanced Vegetation Index (EVI) images and crop curves are processed and evaluated to determine compliance/noncompliance with crop types and planting dates.

10. The non-transitory computer-readable storage medium as recited in claim 8, wherein Normalized Different Tillage Index (NDTI) images and crop curves are processed and evaluated to determine compliance/noncompliance with tillage types and tillage dates.

11. The non-transitory computer-readable storage medium as recited in claim 8, wherein the method further comprises:
for key dates corresponding to implementation and maintenance of a regenerative irrigation practice that comprises one of the regenerative management practices, processing and evaluating remotely sensed visual images against wavelength-based indexes to determine compliance/noncompliance indicators that correspond to each of the key dates.

12. The non-transitory computer-readable storage medium as recited in claim 11, wherein said processing and evaluating remotely sensed visual images against wavelength-based indexes comprises:
detecting colors corresponding to irrigated and non-irrigated fields within a prescribed region corresponding to the parcel, and inferring an amount of irrigation applied to the parcel based upon intensities of the remotely sensed visual images compared to the wavelength-based indices.

13. The non-transitory computer-readable storage medium as recited in claim 8, wherein greenhouse gas emissions for both the baseline and regenerative carbon footprints are calculated by simulating crop growth for 10 years to determine baseline average yearly greenhouse gas emissions and regenerative average yearly greenhouse gas emissions.

14. The non-transitory computer-readable storage medium as recited in claim 13, wherein components of the baseline and regenerative average yearly greenhouse gas emissions comprise average carbon dioxide flux from the soil, nitrous oxide flux from the soil, carbon dioxide from tractor fuel use, and carbon dioxide from production of nitrogen fertilizer.

15. A system for monitoring implementation and maintenance of regenerative management practices in agricultural parcels, the system comprising:
a CO2E sequestration server, comprising a central processing unit (CPU) and a memory, configured to execute an application program disposed in said memory comprising a plurality of code segments, the plurality of code segments comprising:
a CO2E management processor, configured to determine first baseline management practices for a first agricultural parcel and build first simulation inputs that correspond to said first baseline management practices, and configured to determine regenerative management practices for said first agricultural parcel and build second simulation inputs that correspond to said regenerative management practices, wherein said regenerative management practices comprise regenerative tillage practices to improve carbon sequestration;
a crop simulation processor, configured to employ said first simulation inputs to simulate crop growth for said first agricultural parcel fora prescribed number of growing seasons to generate first outputs, and configured to employ said second simulation inputs to simulate crop growth for said first agricultural parcel for said prescribed number of growing seasons to generate second outputs;
a CO2E determination processor, configured to employ said first outputs to compute first average yearly greenhouse gas emissions components and aggregate said first average yearly greenhouse gas emissions components to yield baseline annual carbon dioxide equivalent emissions, and configured to employ said second outputs to compute second average yearly greenhouse gas emissions components and aggregate said second average yearly greenhouse gas emissions components to yield regenerative annual carbon dioxide equivalent emissions, and configured to subtract said baseline annual carbon dioxide equivalent emissions from said regenerative annual carbon dioxide equivalent emissions to yield a first regenerative carbon footprint for the first agricultural parcel;
a client communications processor, configured to communications from a client device indicating acceptance of an offer to implement offered regenerative management practices for said first agricultural parcel; and
a remote sense processor, configured to:
employ remote sensing at a corresponding frequency to infer implementation of said regenerative management practices, wherein:
images having missing data above a prescribed quality threshold are removed;
images having missing data below the prescribed quality threshold are retained;
images not missing data that are time-adjacent to the retained images having missing data are processed by estimating the missing data of the retained images having missing data using the images not missing data that are time-adjacent; and
for a given image of images not missing data and the retained images having missing data that was estimated, relevant spectral bands of said given image are combined to generate composite vegetative indices for subparts of said first agricultural parcel; and
determine that the inferred implementation of the regenerative management practices is compliant with the offered regenerative management practices of the offer;
in response to determining that the inferred implementation of the regenerative management practices is compliant with the offered regenerative management practices of the offer, configured to:
direct said client communications processor to transmit an indication of compliance to a purchaser of carbon credits; and transmit signals that cause payment of an incentive corresponding to said offer for implementing the regenerative management practices.

16. The system as recited in claim 15, wherein said regenerative management practices comprise rotation of crops to improve carbon sequestration, and wherein said CO2E determination processor processes and evaluates Enhanced Vegetation Index (EVI) images and crop curves to determine compliance/noncompliance with crop types and planting dates.

17. The system as recited in claim 15, said CO2E determination processor processes and evaluates Normalized Different Tillage Index (NDTI) images and crop curves to determine compliance/noncompliance with tillage types and tillage dates.

18. The system as recited in claim 15, wherein, for key dates corresponding to implementation and maintenance of a regenerative irrigation practice that comprises one of said regenerative management practices, said CO2E determination processor processes and evaluates remotely sensed visual images against wavelength-based indexes to determine compliance/noncompliance indicators that correspond to each of said key dates.

19. The system as recited in claim 18, wherein said CO2E determination processor processes and evaluates said remotely sensed visual images against wavelength-based indexes by detecting colors corresponding to irrigated and non-irrigated fields within a prescribed region corresponding to said parcel, and infers an amount of irrigation applied to said parcel based upon intensities of said remotely sensed visual images compared to said wavelength-based indices.

20. The system as recited in claim 15, wherein said greenhouse gas emissions for both said baseline and said regenerative carbon footprints are calculated by simulating crop growth for 10 years to determine baseline average yearly greenhouse gas emissions and regenerative average yearly greenhouse gas emissions, and wherein components of said baseline and said regenerative average yearly greenhouse gas emissions comprise average carbon dioxide flux from the soil, nitrous oxide flux from the soil, carbon dioxide from tractor fuel use, and carbon dioxide from production of nitrogen fertilizer.

* * * * *